(12) United States Patent
Sato et al.

(10) Patent No.: US 9,708,292 B2
(45) Date of Patent: Jul. 18, 2017

(54) CYANOPYRIMIDINE DERIVATIVE

(75) Inventors: Norifumi Sato, Osaka (JP); Yohei Yuki, Osaka (JP); Hisashi Shinohara, Osaka (JP); Yasuhiro Takeji, Osaka (JP); Kuni Ito, Osaka (JP); Daisaku Michikami, Osaka (JP); Keisuke Hino, Osaka (JP); Hiroyuki Yamazaki, Osaka (JP)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 741 days.

(21) Appl. No.: 12/865,472

(22) PCT Filed: Feb. 2, 2010

(86) PCT No.: PCT/JP2010/051738
§ 371 (c)(1),
(2), (4) Date: Jul. 30, 2010

(87) PCT Pub. No.: WO2010/090299
PCT Pub. Date: Aug. 12, 2010

(65) Prior Publication Data
US 2012/0022077 A1    Jan. 26, 2012

(30) Foreign Application Priority Data
Feb. 3, 2009   (JP) ................................ 2009-022339

(51) Int. Cl.
*C07D 401/12*   (2006.01)
*A61K 9/08*     (2006.01)
*A61K 31/506*   (2006.01)
*A61K 9/00*     (2006.01)

(52) U.S. Cl.
CPC .......... *C07D 401/12* (2013.01); *A61K 9/0048* (2013.01); *A61K 31/506* (2013.01)

(58) Field of Classification Search
None
See application file for complete search history.

(56) References Cited

U.S. PATENT DOCUMENTS

| | | | |
|---|---|---|---|
| 7,348,306 B2 * | 3/2008 | Araki et al. ................. | 514/20.1 |
| 7,834,002 B2 * | 11/2010 | Kato et al. ............... | 514/217.06 |
| 7,989,446 B2 * | 8/2011 | Kato et al. ............... | 514/217.06 |
| 2004/0176417 A1 | 9/2004 | Rosentreter et al. | |
| 2006/0154969 A1 | 7/2006 | Rosentreter et al. | |
| 2007/0140897 A1 | 6/2007 | Wang et al. | |
| 2008/0182854 A1 | 7/2008 | Kato et al. | |

FOREIGN PATENT DOCUMENTS

| | | |
|---|---|---|
| JP | 2007-145828 A | 6/2007 |
| RU | 2006 102 955 A | 7/2004 |
| WO | WO 02/070485 A1 | 9/2002 |
| WO | WO 03/008384 A1 | 1/2003 |
| WO | WO 2005/003099 A2 | 1/2005 |
| WO | WO 2005/105778 A2 | 11/2005 |

OTHER PUBLICATIONS

International Search Report from the European Patent Office for International Application No. PCT/JP2010/051738, mailing date May 11, 2010.
International Preliminary Report on Patentability dated Aug. 11, 2011 issued in corresponding International Application No. PCT/JP2010/051738.
Search Report for Counterpart CN Application No. 201080006492.5 issued May 17, 2013.
Office Action for Counterpart CN Application No. 201080008492.5 issued May 17, 2013.

* cited by examiner

*Primary Examiner* — Leslie A. Royds Draper
(74) *Attorney, Agent, or Firm* — Finnegan, Henderson, Farabow, Garrett & Duner, LLP

(57) ABSTRACT

The present invention relates to a novel cyanopyrimidine compound and a pharmaceutical composition which have a safe and potent adenosine A2a receptor agonistic activity.

13 Claims, 3 Drawing Sheets

Effects of Example 1 on Ciliary Artery in Rabbits

Data = Mean ± SE (n=6)

Effect of Example 1 on Cell Survival in Rat Retinal Ganglion Cell

DATA=Mean±SE (n=8)

CYANOPYRIMIDINE DERIVATIVE

TECHNICAL FIELD

The present invention relates to a novel cyanopyrimidine compound, and a pharmaceutical composition and formulation comprising the compound.

BACKGROUND ART

Adenosine is a substance that may exhibit various physiological actions when it binds to a receptor on a cell surface. The adenosine receptor on the cell surface belongs to G-protein-coupled receptor family, and it is classified into A1, A2a, A2b and A3. Among them, the adenosine A1 and adenosine A3 receptors are coupled with Gi-protein and the activation thereof results in lowering of the intracellular c-AMP level. In addition, adenosine A2a and adenosine A2b receptors are coupled with Gs-protein and the activation thereof results in heightening of the intracellular c-AMP level. These 4 kinds of adenosine receptor subtypes each have been cloned.

A variety of studies about agonists and antagonists which may work on each of the above adenosine receptor subtypes have been already reported. Among them, the adenosine A2a receptor agonists have been reported not only to exhibit the potent antihypertensive action and to be useful as above-mentioned drugs such as an antihypertensive drug, a medicament for treating/preventing cardiac or cerebral ischemic disease and antiarteriosclerotic drug, but also to exhibit an ocular hypotensive action (see J. Pharmcol. Exp. Ther. 320-326, 273 (1995).

WO 2005/105778 discloses cyanopyrimidine compounds which are an adenosine A2a receptor agonist. However, WO 2005/105778 does not disclose any specific cyanopyrimidine compounds like the present invention.

DISCLOSURE OF INVENTION

Problem to be Solved by the Invention

An object of the present invention is to provide a novel compound having a safe and potent adenosine A2a receptor agonistic activity.

Means to Solve the Problem

The present inventors have extensively studied to reach for the above object, and have found that the following compounds exhibited a potent adenosine A2a receptor agonistic action as well as an excellent safety. In addition, the present inventors have also found that the following compounds exhibited vascular relaxation for ocular ciliary artery and neuroprotection on retinal ganglion cell. The present invention has been completed by the additional studies based on these findings.

The present invention provides a cyanopyrimidine compound shown in the following Term 1, a composition and formulation comprising the compound, use of the compound, a method for treating or preventing a disease, and a process for the compound.

Term 1. A cyanopyrimidine compound of formula (1):

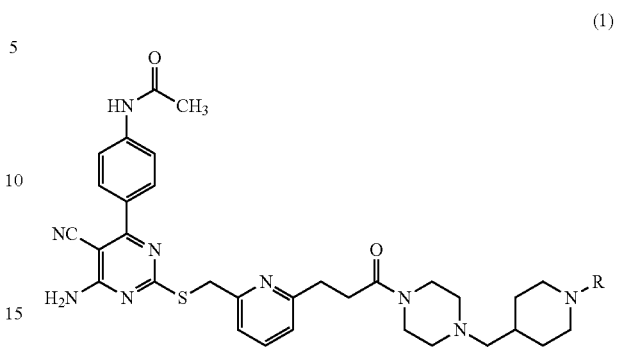

(1)

wherein R is hydrogen, hydroxy (lower alkyl) group, halogenated (lower alkyl) group or (lower alkoxy)carbonyl-(lower alkyl) group
or a salt thereof.

Term 2. The cyanopyrimidine compound of term 1 which is selected from the group consisting of
(1) N-(4-(6-amino-5-cyano-2-((6-(3-oxo-3-(4-(piperidin-4-ylmethyl)piperazin-1-yl)propyl)pyridin-2-yl)methylthio)-pyrimidin-4-yl)phenyl)acetamide,
(2) N-(4-(6-amino-5-cyano-2-((6-(3-(4-((1-(2-hydroxyethyl)-piperidin-4-yl)methyl)piperazin-1-yl)-3-oxopropyl)pyridin-2-yl)methylthio)pyrimidin-4-yl)phenyl)acetamide,
(3) N-(4-(6-amino-5-cyano-2-((6-(3-(4-((1-(3-hydroxy-propyl)piperidin-4-yl)methyl)piperazin-1-yl)-3-oxopropyl)-pyridin-2-yl)methylthio)pyrimidin-4-yl)phenyl)acetamide,
(4) N-(4-(6-amino-5-cyano-2-((6-(3-(4-((1-(2-fluoroethyl)-piperidin-4-yl)methyl)piperazin-1-yl)-3-oxopropyl)pyridin-2-yl)methylthio)pyrimidin-4-yl)phenyl)acetamide, and
(5) N-(4-(6-amino-5-cyano-2-((6-(3-(4-((1-(2-methoxy-carbonylethyl)piperidin-4-yl)methyl)piperazin-1-yl)-3-oxopropyl)pyridin-2-yl)methylthio)pyrimidin-4-yl)phenyl)-acetamide,
or a salt thereof.

Term 3. A pharmaceutical composition comprising the compound of term 1 or 2 or a salt thereof, and a pharmaceutically acceptable carrier.

Term 4. The pharmaceutical composition of term 3 for treating or preventing an eye disease.

Term 5. The pharmaceutical composition of term 4 for treating or preventing glaucoma.

Term 6. Use of the compound of term 1 or 2 or a salt thereof as adenosine A2a receptor agonist.

Term 7. A method for treating an eye disease which comprises administering an effective amount of the compound of term 1 or 2 or a salt thereof to an animal or human being in need of such treatment.

Term 8. An aqueous liquid preparation comprising the pharmaceutical composition of term 3.

Term 9. The aqueous liquid preparation of term 8 which further comprises one of more additives selected from a pharmaceutically acceptable buffer, isotonic agent, preservative, solubilizer and pH adjuster.

Term 10. The aqueous liquid preparation of term 9 wherein the buffer is selected from succinic acid, boric acid, phosphoric acid and amino acid, and a pharmaceutically acceptable salt thereof.

Term 11. The aqueous liquid preparation of term 10 wherein the buffer is succinic acid.

Term 12. The aqueous liquid preparation of term 8 wherein the isotonic agent is one or two isotonic agents selected from glucose, sorbitol, mannitol, sodium chloride, potassium chloride, propylene glycol and glycerin.

Term 13. The aqueous liquid preparation of term 9 wherein the preservative is selected from benzalkonium chloride, benzethonium chloride, benzododecinium bromide, chlorhexidine gluconate, methyl para-oxybenzoate, propyl para-oxybenzoate, chlorobutanol and benzyl alcohol.

Term 14. The aqueous liquid preparation of any one of terms 8 to 13 wherein the pH is about 5.0 to 9.0.

Each group defined in the above-mentioned general formula is specifically meant as follows.

The halogen atom herein used includes fluorine, chlorine, bromine and iodine atoms.

The (lower alkoxy)carbonyl group herein used includes an alkoxycarbonyl group wherein the alkoxy moiety is a straight or branched chain alkoxy group containing 1 to 6 carbons. In more detail, it includes, for example, methoxycarbonyl, ethoxycarbonyl, n-propoxycarbonyl, isopropoxycarbonyl, n-butoxycarbonyl, isobutoxycarbonyl, tert-butoxycarbonyl, sec-butoxycarbonyl, n-pentyloxycarbonyl, neopentyloxycarbonyl, n-hexyloxycarbonyl, isohexyloxycarbonyl, 3-methylpentyloxycarbonyl, etc.

The halogenated (lower alkyl) group herein used includes a lower alkyl group (preferably a straight or branched chain alkyl group containing 1 to 6 carbons) substituted with 1 to 7 halogen atoms, preferably 1 to 3 halogen atoms. In more detail, it includes, for example, fluoromethyl, difluoromethyl, trifluoromethyl, chloromethyl, dichloromethyl, trichloromethyl, bromomethyl, dibromomethyl, dichlorofluoromethyl, 2,2-difluoroethyl, 2,2,2-trifluoroethyl, pentafluoroethyl, 2-fluoroethyl, 2-chloroethyl, 3,3,3-trifluoropropyl, heptafluoropropyl, 2,2,3,3,3-pentafluoropropyl, heptafluoroisopropyl, 3-chloropropyl, 2-chloropropyl, 3-bromopropyl, 4,4,4-trifluorobutyl, 4,4,4,3,3-pentafluorobutyl, 4-chlorobutyl, 4-bromobutyl, 2-chlorobutyl, 5,5,5-trifluoropentyl, 5-chloropentyl, 6,6,6-trifluorohexyl, 6-chlorohexyl, perfluorohexyl, etc.

The hydroxy (lower alkyl) group herein used includes the above-mentioned lower alkyl group (preferably a straight or branched chain alkyl group containing 1 to 6 carbons) substituted with 1 to 5 hydroxy groups, preferably 1 to 3 hydroxy groups. In more detail, it includes, for example, hydroxymethyl, 2-hydroxyethyl, 1-hydroxyethyl, 3-hydroxypropyl, 2,3-dihydroxypropyl, 4-hydroxybutyl, 3,4-dihydroxybutyl, 1,1-dimethyl-2-hydroxyethyl, 5-hydroxypentyl, 6-hydroxyhexyl, 3,3-dimethyl-3-hydroxypropyl, 2-methyl-3-hydroxypropyl, 2,3,4-trihydroxybutyl, perhydroxy-hexyl, etc.

The (lower alkoxy)carbonyl lower alkyl group used herein includes the above-mentioned lower alkyl group (preferably a straight or branched chain alkyl group containing 1 to 6 carbons) having 1 to 3 (preferably 1 to 2) of the above-mentioned (lower alkoxy)carbonyl groups (preferably straight or branched chain alkoxycarbonyl groups containing 1 to 6 carbons). In more detail, it includes, for example, methoxycarbonylmethyl, ethoxycarbonylmethyl, 1-methoxycarbonylethyl, 2-methoxy-carbonylethyl, 2-ethoxycarbonylethyl, 1-ethoxycarbonylethyl, 2-tert-butoxycarbonylethyl, 3-methoxycarbonylpropyl, 3-ethoxycarbonylpropyl, 4-ethoxycarbonylbutyl, 5-isopropoxy-carbonylpentyl, 6-n-propoxycarbonylhexyl, 1,1-dimethyl-2-n-butoxycarbonylethyl, 1-methyl-1-methoxycarbonylethyl, 2-methyl-1-methoxycarbonylpropyl, 2-methyl-3-tert-butoxy-carbonylpropyl, 3-methyl-1-methoxycarbonylbutyl, diethoxy-carbonylmethyl, 1,2-diethoxycarbonylethyl, 2-n-pentyloxy-carbonylethyl, n-hexyloxycarbonylmethyl, etc.

The pyrimidine derivatives denoted in the above-mentioned general formula (1) can be prepared by various means. As an example, the derivatives can be prepared according to the following schemes 1 to 4.

Scheme 1

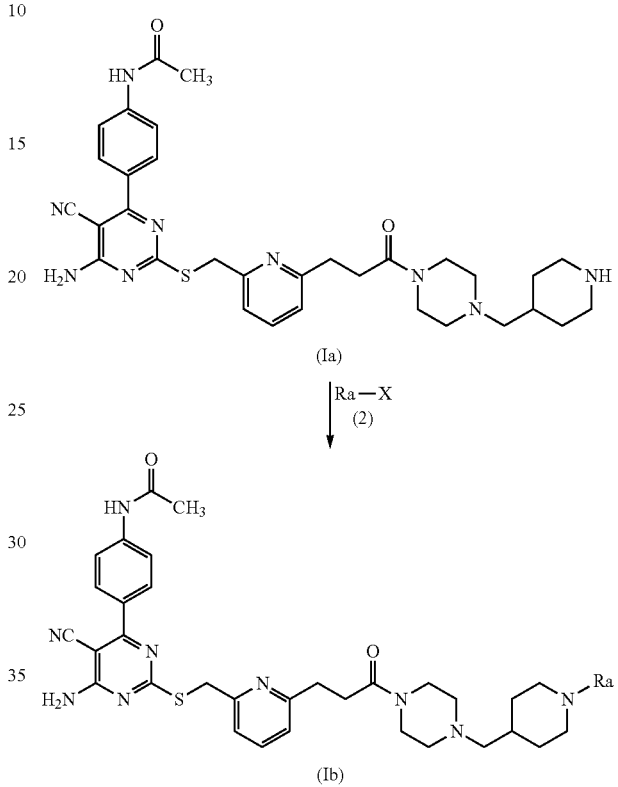

Wherein Ra is a hydroxy(lower alkyl) group, a halogenated (lower alkyl) group or a (lower alkoxy)carbonyl(lower alkyl) group; X is a halogen atom or a group which can perform a substitution reaction like a halogen atom.

The halogen atom which is denoted as X in the compound of formula (2) includes fluorine, chlorine, bromine, and iodine atoms.

The group which can perform a substitution reaction like a halogen atom, denoted as X, includes, for example, a leaving group such as a (lower alkane)sulfonyloxy group, and an arylsulfonyloxy group.

The (lower alkane)sulfonyloxy group herein used includes a straight or branched chain alkanesulfonyloxy group containing 1 to 6 carbons; in more detail, it includes, for example, methanesulfonyloxy, ethane-sulfonyloxy, isopropanesulfonyloxy, n-propanesulfonyloxy, n-butanesulfonyloxy, tert-butanesulfonyloxy, n-pentane-sulfonyloxy, n-hexanesulfonyloxy, etc.

The arylsulfonyloxy group herein used includes, for example, phenylsulfonyloxy group, naphthylsulfonyloxy group, etc. The phenyl may have 1 to 3 substituents selected from the group consisting of, for example, a straight or branched chain alkyl group containing 1 to 6 carbons, a straight or branched chain alkoxy group containing 1 to 6 carbons, nitro group, and a halogen atom. Specific examples of the arylsulfonyloxy group include, for example, phenylsulfonyloxy, 4-methylphenylsulfonyloxy, 2-methylphenylsulfonyloxy, 4-nitrophenylsulfonyloxy, 4-methoxy-phenylsulfonyloxy, 2-nitrophenylsulfonyloxy, 3-chlorophenylsulfonyloxy, etc. Specific examples of the naphthylsulfonyloxy group includes, for example, a-naphthylsulfonyloxy, β-naphthylsulfonyloxy, etc.

The compound of formula (1b) can be prepared by reacting Compound (1a) and Compound (2).

The reaction is generally carried out in a conventional solvent which does not adversely affect the reaction, for example, water; an alcohol solvent such as methanol, ethanol, isopropanol, n-butanol, trifluoroethanol, and ethylene glycol; a ketone solvent such as acetone and methyl ethyl ketone; an ether solvent such as tetrahydrofuran, dioxane, diethyl ether, and diglyme; an ester solvent such as methyl acetate and ethyl acetate; an aprotic polar solvent such as acetonitrile, N,N-dimethylformamide, and dimethylsulfoxide; a halogenated hydrocarbon solvent such as methylene chloride and ethylene chloride; or other organic solvents. In addition, the reaction may be carried out in a mixture of the above-mentioned conventional solvents.

The above-mentioned reactions are generally carried out in the presence of a basic compound. The basic compound includes a general inorganic base and organic base.

The inorganic base herein used includes, for example, alkali metal such as sodium and potassium; alkali metal hydrogen carbonate such as lithium hydrogen carbonate, sodium hydrogen carbonate and potassium hydrogen carbonate; alkali metal hydroxide such as lithium hydroxide, sodium hydroxide, potassium hydroxide and cesium hydroxide; alkali metal carbonate such as lithium carbonate, sodium carbonate, potassium carbonate and cesium carbonate; alkali metal (lower alkoxide) such as sodium methoxide and sodium ethoxide; alkali metal hydride compound such as sodium hydride and potassium hydride; etc.

The organic base herein used includes, for example, trialkylamine such as trimethylamine, triethylamine and N-ethyl-diisopropylamine; pyridine; quinoline; piperidine; imidazole; picoline; dimethylaminopyridine; dimethylaniline; N-methylmorpholine; 1,5-diazabicyclo[4.3.0]non-5-ene (DBN); 1,4-diazabicyclo[2.2.2]octane (DABCO); 1,8-diazabicyclo[5.4.0]undec-7-ene (DBU); etc.

The basic compound may be used as a single ingredient or in any combination of two or more ingredients.

The amount of the basic compound herein used is generally 0.5 to 10 times mole of Compound (1a), preferably 0.5 to 6 times mole of compound (1a). The basic compound can be also used as a solvent when it is liquid.

The above reaction media may include as a reaction accelerant an alkali metal iodide such as potassium iodide and sodium iodide where appropriate.

The ratio between Compound (1a) and Compound (2) used in the above Scheme 1 is at least 1 mole, preferably 1 to 5 mole of Compound (2) per 1 mole of Compound (1a).

The reaction temperature is not limited, and the reaction can be generally performed under cooling, at room temperature or under heating. Preferably, the above reaction may be carried out around at room temperature for 1 to 30 hours.

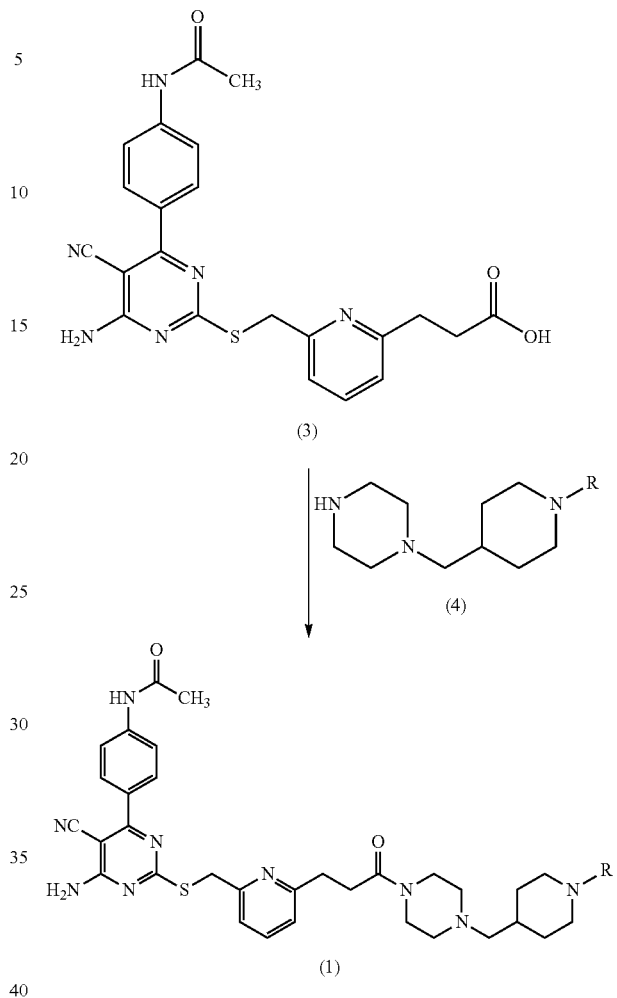

Wherein R is as defined above.

Compound (1) can be prepared by reacting Compound (3) or a reactive derivative thereof whose carboxyl group is activated, and Compound (4) or a reactive derivative thereof whose imino group is activated.

The preferable reactive form of the carboxylic group in Compound (3) includes an acid halide, an acid anhydride, an active amide, an active ester, etc. The preferable examples of the reactive form of the carboxylic group include an acid chloride; an acid azide; a mixed anhydride of a substituted phosphoric acid (e.g. dialkyl phosphoric acid, phenyl phosphoric acid, diphenyl phosphoric acid, dibenzyl phosphoric acid, and halogenated phosphoric acid), a dialkylphosphorous acid, a sulfurous acid, a thiosulfuric acid, a sulfuric acid, a sulfonic acid (e.g. methanesulfonic acid), an aliphatic acid (e.g. acetic acid, propionic acid, butyric acid, isobutyric acid, pivalic acid, pentanoic acid, isopentanoic acid, 2-ethylbutyric acid, trichloroacetic acid) or aromatic acid (e.g. benzoic acid); symmetry acid anhydride; an active amide of imidazole, 4-substituted imidazole, dimethylpyrazole, triazole or tetrazole; an active ester (e.g. cyanomethyl ester, methoxymethyl ester, dimethyliminomethyl ester, vinyl ester, propargyl ester, p-nitrophenyl ester, 2,4-dinitrophenyl ester, trichlorophenyl ester, pentachlorophenyl ester, mesylphenyl ester, etc.) or an ester with an N-hydroxy compound (e.g. N,N-dimethylhydroxylamine, 1-hydroxy-2-(1H)-pyridone, N-hydroxysuccinimide, N-hydroxyphthalimide, 1-hydroxy-1H-benzotriazole, etc.). It is possible to select any moderate compound from these reactive derivatives depending on the type of Compound (3) to be used.

In case that Compound (3) is used as a free acid or a salt thereof in the above reaction, the reaction can be preferably carried out in the presence of a condensing agent. The condensing agent includes a conventional and well-known one, for example, N,N'-dichlorohexyl-carbodiimide; N-cyclohexyl-N'-morpholinoethylcarbodiimide; N-cyclohexyl-N'-(4-diethylaminocyclohexyl)carbodiimide; N,N'-diethylcarbodiimide; N,N'-diisopropylcarbodiimide; N-ethyl-N'-(3-dimethylaminopropyl)carbodiimide or a hydrochloride thereof; N,N'-carbonyl bis(2-methyl-imidazole); pentamethyleneketene-N-cyclohexylimine; diphenylketene-N-cyclohexylimine; ethoxyacetylene, 1-alkoxy-1-chloroethylene; trialkyl phosphite; ethyl polyphosphate; isopropyl polyphosphate; phosphorus oxychloride (sulfonyl chloride); phosphorus trichloride; diphenyl sulfonyl azide; thionyl chloride; oxalyl chloride; a (lower alkyl) haloformate (e.g. ethyl chloroformate, isopropyl chloroformate, etc.); triphenylphosphine; 2-ethyl-7-hydroxybenzisoxazolium salt; 2-ethyl-5-(m-sulfophenyl)isoxazolium hydroxide inner salt; benzotriazol-1-yloxy-tris-(dimethylamino)phosphonium hexafluorophosphate; 1-(p-chlorobenzenesulfonyloxy)-6-chloro-1H-benzotriazole; Vilsmeier reagent which is prepared by reacting N,N-dimethylformamide with thionyl chloride, phosgene, trichloromethyl chloroformate, phosphorus oxychloride, etc. More preferably, the reaction is carried out in the presence of the above-mentioned condensing agent, and in connection with an active-esterification agent such as N-hydroxysuccinimide, N-hydroxyphthalimide, and 1-hydroxy-1H-benzotriazole.

The preferable reactive derivative of the imino group in Compound (4) includes a Schiff base-type imino group or an enamine-type tautomer thereof which is generated by reacting Compound (4) and a carbonyl compound such as aldehyde and ketone; a silyl derivative which is generated by reacting Compound (4) and a silyl compound such as bis(trimethylsilyl)acetamide, mono(trimethylsilyl)acetamide, and bis(trimethylsilyl)urea; a derivative which is generated by reacting Compound (4), and phosphorus trichloride, phosgene, etc.

The reaction is generally carried out in a conventional solvent which does not adversely affect the reaction, for example, water; an alcohol solvent such as methanol, ethanol, isopropanol, n-butanol, trifluoroethanol, and ethylene glycol; a ketone solvent such as acetone and methyl ethyl ketone; an ether solvent such as tetrahydrofuran, dioxane, diethyl ether, diisopropyl ether, and diglyme; an ester solvent such as methyl acetate and ethyl acetate; an aprotic polar solvent such as acetonitrile, N,N-dimethylformamide, and dimethylsulfoxide; a hydrocarbon solvent such as n-pentane, n-hexane, n-heptane, and cyclohexane; a halogenated hydrocarbon solvent such as methylene chloride and ethylene chloride; or other organic solvents. In addition, the reaction may be carried out in a mixture of the above-mentioned conventional solvents.

The above reaction may be carried out in the presence of a base. The base includes a variety of known inorganic or organic bases. The inorganic base herein used includes, for example, alkali metal such as sodium and potassium; alkali metal hydrogen carbonate such as lithium hydrogen carbonate, sodium hydrogen carbonate and potassium hydrogen carbonate; alkali metal hydroxide such as lithium hydroxide, sodium hydroxide, potassium hydroxide and cesium hydroxide; alkali metal carbonate such as lithium carbonate, sodium carbonate, potassium carbonate and cesium carbonate; alkali metal lower alkoxide such as sodium methoxide and sodium ethoxide; alkali metal hydride compound such as sodium hydride and potassium hydride; etc. The organic base herein used includes, for example, trialkylamine such as trimethylamine, triethylamine and N-ethyl diisopropylamine; pyridine; quinoline; piperidine; imidazole; picoline; dimethylaminopyridine; dimethylaniline; N-methylmorpholine; 1,5-diazabicyclo[4.3.0]non-5-ene (DEN); 1,4-diazabicyclo-[2.2.2]octane (DABCO); 1,8-diazabicyclo[5.4.0]undec-7-ene (DBU); etc. And, the base can be also used as a solvent when it is liquid. The base may be used as a single ingredient or in any combination of two or more ingredients. The amount of the basic compound herein used is generally 0.1 to 10 mole per 1 mole of Compound (3), preferably 0.1 to 3 mole per 1 mole of Compound (3).

The ratio between Compound (3) and Compound (4) used in the above Scheme 2 is at least 1 mole, preferably 1 to 5 mole of Compound (3) per 1 mole of Compound (4).

The reaction temperature is not limited, and the reaction can be generally performed under cooling, at room temperature or under heating. Preferably, the above reaction may be carried out at room temperature to 100° C. for 30 minutes to 30 hours, preferably 30 minutes to 5 hours.

Compound (3) used as a starting material in the above reaction is a known compound, and the process of the compound is described below (Scheme 4).

Scheme 3

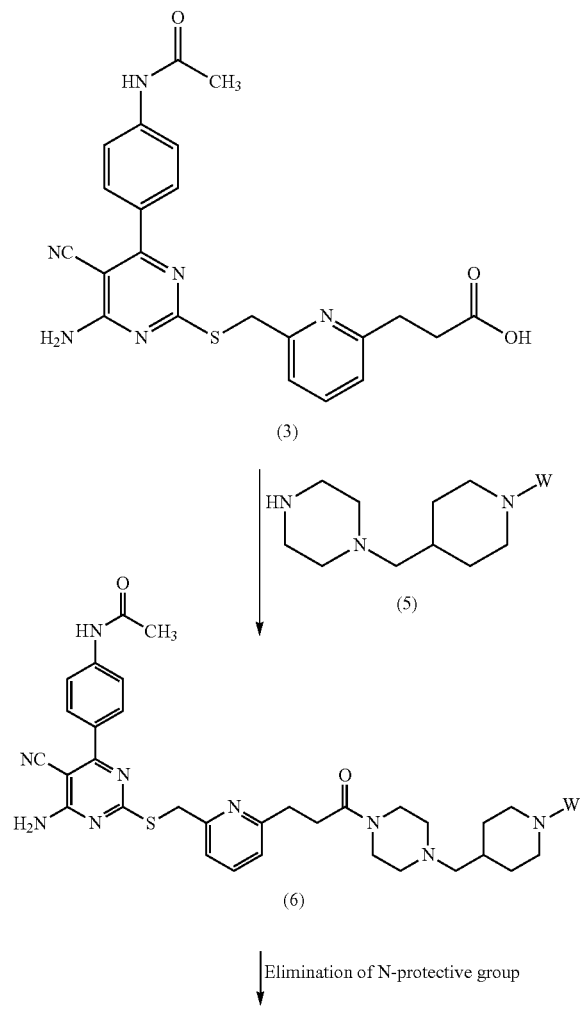

-continued

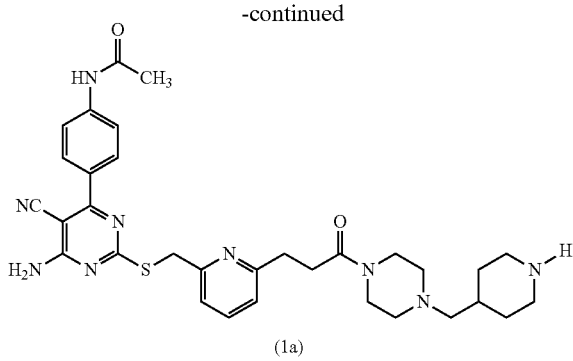

(1a)

Wherein W is N-protective group.

Compound (6) can be prepared by reacting Compound (3) and Compound (5) in a similar manner to Scheme 2. Further Compound (1a) can be prepared by the elimination of the N-protective group.

The N-protective group herein used as W includes, for example, a (lower alkoxy)carbonyl group, a lower alkanoyl group, an aryl-substituted (lower alkyl) group, etc.

The (lower alkoxy)carbonyl group herein used includes a straight or branched chain alkoxycarbonyl group containing 1 to 6 carbons, for example, methoxycarbonyl, ethoxycarbonyl, propoxycarbonyl, butoxycarbonyl, tert-butoxycarbonyl, pentyloxycarbonyl, hexyloxycarbonyl, etc.

The lower alkanoyl group herein used includes a straight or branched chain alkanoyl group containing 1 to 6 carbons, for example, formyl, acetyl, propionyl, butyryl, isobutyryl, pentanoyl, tert-butylcarbonyl, hexanoyl, etc.

The aryl-substituted (lower alkyl) group herein used includes, for example, benzyl, 2-phenylethyl, 1-phenylethyl, 3-phenylpropyl, 4-phenylbutyl, 5-phenylpentyl, 6-phenylhexyl, diphenylmethyl, trityl, etc., and a straight or branched chain alkyl group containing 1 to 6 carbons which is substituted with 1 to 3 phenyl groups. The substituent on the phenyl groups includes, for example, a straight or branched chain alkyl group containing 1 to 6 carbons which may be optionally substituted with 1 to 3 groups selected from the group consisting of halogen atom and hydroxy group (e.g. methyl, ethyl, propyl, n-butyl, sec-butyl, tert-butyl, n-pentyl, n-hexyl, hydroxymethyl, 2-hydroxyethyl, 1-hydroxyethyl, 3-hydroxypropyl, 2,3-dihydroxypropyl, 4-hydroxybutyl, 1,1-dimethyl-2-hydroxyethyl, 5,5,4-trihydroxypentyl, 5-hydroxypentyl, 6-hydroxyhexyl, 1-hydroxyisopropyl, 2-methyl-3-hydroxypropyl, trifluoromethyl, trichloromethyl, chloromethyl, bromomethyl, fluoromethyl, iodomethyl, difluoromethyl, dibromomethyl, 2-chloroethyl, 2,2,2-trifluoroethyl, 2,2,2-trichloroethyl, 3-chloropropyl, 2,3-dichloropropyl, 4,4,4-trichlorobutyl, 4-fluorobutyl, 5-chloropentyl, 3-chloro-2-methylpropyl, 5-bromohexyl, 5,6-dichlorohexyl, 3-hydroxy-2-chloropropyl, etc.); a straight or branched chain alkoxy group containing 1 to 6 carbons which may be optionally substituted with 1 to 3 groups selected from the group consisting of halogen atom and hydroxy group (e.g. methoxy, ethoxy, propoxy, n-butoxy, sec-butoxy, tert-butoxy, n-pentyloxy, n-hexyloxy, hydroxymethoxy, 2-hydroxyethoxy, 1-hydroxyethoxy, 3-hydroxypropoxy, 2,3-dihydroxypropoxy, 4-hydroxybutoxy, 1,1-dimethyl-2-hydroxyethoxy, 5,5,4-trihydroxypentyloxy, 5-hydroxypentyloxy, 6-hydroxyhexyloxy, 1-hydroxyisopropoxy, 2-methyl-3-hydroxypropoxy, trifluoromethoxy, trichloro-methoxy, chloromethoxy, bromomethoxy, fluoromethoxy, iodomethoxy, difluoromethoxy, dibromomethoxy, 2-chloro-ethoxy, 2,2,2-trifluoroethoxy, 2,2,2-trichloroethoxy, 3-chloropropoxy, 2,3-dichloropropoxy, 4,4,4-trichlorobutoxy, 4-fluorobutoxy, 5-chloropentyloxy, 3-chloro-2-methylpropoxy, 5-bromohexyloxy, 5,6-dichlorohexyloxy, 3-hydroxy-2-chloropropoxy, etc.); and a halogen atom (e.g. fluorine, bromine, chlorine, iodine atoms). In case that there are 2 or more substituents on the phenyl group, the substituents may be identical or different.

The elimination of N-protective group: W can be carried out via a conventional manner such as hydrolysis and hydrogenation. The reaction is generally carried out in a conventional solvent which does not adversely affect the reaction, for example, water; an alcohol solvent such as methanol, ethanol, isopropanol, n-butanol, trifluoroethanol, and ethylene glycol; a ketone solvent such as acetone and methyl ethyl ketone; an ether solvent such as tetrahydrofuran, dioxane, diethyl ether, dimethoxyethane, and diglyme; an ester solvent such as methyl acetate and ethyl acetate; an aprotic polar solvent such as acetonitrile, N,N-dimethylformamide, dimethylsulfoxide and N-methylpyrrolidone; a halogenated hydrocarbon solvent such as methylene chloride and ethylene chloride; or other organic solvents. In addition, the reaction may be carried out in a mixture of the above-mentioned conventional solvents.

(i) Hydrolysis:

The hydrolysis is preferably carried out in the presence of a base or an acid including a Lewis acid.

The base herein used includes conventional inorganic bases and organic bases. The preferable inorganic base includes, for example, an alkali metal such as sodium and potassium; an alkaline earth metal such as magnesium and calcium; and a hydroxide, carbonate or hydrogen carbonate of the alkali metal or the alkaline earth metal. The preferable organic base includes, for example, a trialkylamine such as trimethylamine and triethylamine; picoline; 1,5-diazabicyclo[4,3,0]non-5-ene; etc.

The acid herein used includes conventional organic acids and inorganic acids. The preferable organic acid includes, for example, an aliphatic acid such as formic acid, acetic acid and propionic acid; and trihaloacetic acid such as trichloroacetic acid and trifluoroacetic acid. The preferable inorganic acid includes, for example, hydrochloric acid, hydrobromic acid, sulfuric acid, hydrogen chloride, hydrogen bromide, etc. The Lewis acid herein used includes, for example, boron trifluoride etherate, boron tribromide, aluminium chloride, ferric chloride, etc.

In case that trihaloacetic acid or a Lewis acid is used as an acid, the reaction is preferably carried out in the presence of a cation scavenger such as anisole and phenol.

The amount of the base or acid herein used is not limited as long as the amount is enough for the hydrolysis.

The reaction temperature is generally 0 to 120° C., preferably room temperature to 100° C., and more preferably room temperature to 80° C. The reaction time is generally 30 minutes to 24 hours, preferably 30 minutes to 12 hours, and more preferably 1 to 8 hours.

(ii) Hydrogenation:

The hydrogenation herein used can be carried out by means of a conventional/known hydrogenation. The conventional hydrogenation includes, for example, chemical reduction, catalytic reduction, etc.

The preferable reducing agent used in the chemical reduction includes a hydride such as hydrogen iodide, hydrogen sulfide, lithium aluminium hydride, sodium borohydride and sodium cyanoborohydride; or a metal such as tin, zinc and iron; or a combination of a metal compound (e.g. chromium chloride, chromium acetate, etc.) and an organic or inorganic acid (e.g. formic acid, acetic acid, propionic acid, trifluoroacetic acid, p-toluenesulfonic acid, hydrochloric acid, hydrobromic acid, etc.).

The reaction temperature is generally 0 to 120° C., preferably room temperature to 100° C., and more preferably room temperature to 80° C. The reaction time is generally 30 minutes to 24 hours, preferably 30 minutes to 10 hours, and more preferably 30 minutes to 4 hours.

Scheme 4

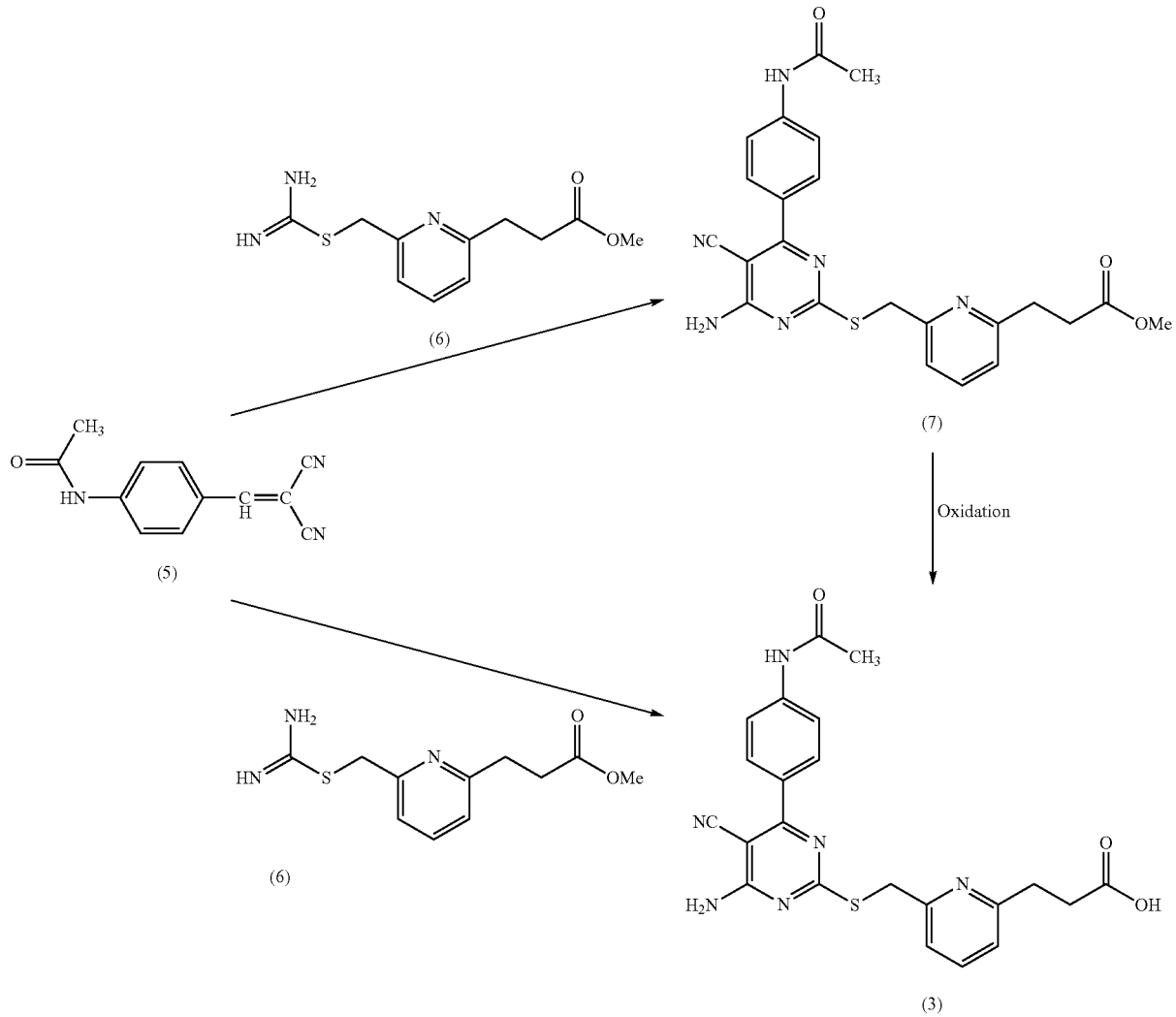

The preferable catalyst used in the catalytic reduction includes a platinum catalyst such as platinum plate, spongiform platinum, platinum black, colloidal platinum, platinum dioxide, and platinum wire; a palladium catalyst such as spongiform palladium, palladium black, palladium oxide, palladium carbon, palladium/barium sulfate, and palladium/barium carbonate; a nickel catalyst such as reduced nickel, nickel oxide, and Raney nickel; a cobalt catalyst such as reduced cobalt, and Raney cobalt; an iron catalyst such as reduced iron; etc.

The acid used in the chemical reduction can be also used as a solvent when it is liquid.

The amount of the reducing agent or the catalyst used in the catalytic reduction may be, but not limited, a generally-used amount.

Compound (3) can be prepared by reacting Compound (5) and Compound (6). The reaction is carried out according to the reference (El-Sharabsy, S. A.; Abdel Gawad, S. M.; Hussain, S. M.; J. Prakt. Chem., 1989, 331 (2), 207) or a similar method thereto.

The reaction is generally carried out in a conventional solvent which does not adversely affect the reaction, for example, water; an alcohol solvent such as methanol, ethanol, isopropanol, n-butanol, trifluoroethanol, and ethylene glycol; a ketone solvent such as acetone and methyl ethyl ketone; an ether solvent such as tetrahydrofuran, dioxane, diethyl ether, and diglyme; an ester solvent such as methyl acetate and ethyl acetate; an aprotic polar solvent such as acetonitrile, N,N-dimethylformamide, and dimethylsulfoxide; a halogenated hydrocarbon solvent such as methylene chloride and ethylene chloride; or other organic solvents. In addition, the reaction may be carried out in a mixture of the above-mentioned conventional solvents.

The above reaction can be carried out without a catalytic compound or in the presence of an acid catalyst. Generally, the reaction is preferably carried out in the presence of a basic compound. The basic compound includes general inorganic and organic bases.

The inorganic base herein used includes, for example, alkali metal such as sodium and potassium; alkali metal hydrogen carbonate such as lithium hydrogen carbonate, sodium hydrogen carbonate and potassium hydrogen carbonate; alkali metal hydroxide such as lithium hydroxide, sodium hydroxide, potassium hydroxide and cesium hydroxide; alkali metal carbonate such as lithium carbonate, sodium carbonate, potassium carbonate and cesium carbonate; alkali metal (lower alkoxide) such as sodium methoxide and sodium ethoxide; alkali metal hydride compound such as sodium hydride and potassium hydride; etc.

The organic base herein used includes, for example, trialkylamine such as trimethylamine, triethylamine and N-ethyl diisopropylamine; pyridine; quinoline; piperidine; imidazole; picoline; dimethylaminopyridine; dimethylaniline; N-methylmorpholine; DBN, DABCO, DBU; etc.

The basic compound may be used as a single ingredient or in any combination of two or more ingredients.

The amount of the basic compound herein used is generally a catalytic amount to 10 times mole of Compound (5), preferably equivalent mole to 3.5 times mole of Compound (5). The basic compound can be also used as a solvent when it is liquid.

The ratio between Compound (6) and Compound (5) is at least 1 mole per 1 mole of Compound (6), preferably 1 to 5 mole of Compound (5) per 1 mole of Compound (6).

The reaction temperature is not limited, and the reaction can be generally performed under cooling, at room temperature or under heating. Preferably, the above reaction may be carried out under reflux for 1 to 30 hours.

When the dihydro-form Compound (7) as an intermediate is produced in the reaction, Compound (7) can be further oxidated to give Compound (8).

The oxidation of Compound (7) can be carried out via a conventional method used in the technical field. The preferable oxidating agent includes, for example, 2,3-dichloro-5,6-dicyano-p-benzoquinone (DDQ), N-bromosuccinimide (NBS), etc.

The oxidation reaction is generally carried out neat or in a conventional solvent which does not adversely affect the reaction, for example, an alcohol solvent such as methanol, ethanol, isopropanol, n-butanol, trifluoroethanol, and ethylene glycol; a ketone solvent such as acetone and methyl ethyl ketone; an ether solvent such as tetrahydrofuran, dioxane, diethyl ether, and diglyme; an ester solvent such as methyl acetate and ethyl acetate; an aprotic polar solvent such as acetonitrile, N,N-dimethylformamide, and dimethylsulfoxide; a halogenated hydrocarbon solvent such as methylene chloride and ethylene chloride; or other organic solvents. In addition, the reaction may be carried out in a mixture of the above-mentioned conventional solvents.

The amount of the oxidizing agent herein used is generally a catalytic amount to excess mole of Compound (7).

The reaction temperature is not limited, and the reaction can be generally performed under cooling, at room temperature or under heating. Preferably, the above reaction may be carried out under reflux for 0.5 to 75 hours.

Compound (7) in the above Scheme 4 includes an isomer about the double-bond site in the ring.

Compound (4) used as a starting material is an available known compound.

The starting material used in the above scheme may be an appropriate salt thereof, and the desired compounds in each reaction may be also appropriate salts.

The desired compounds of each process shown in above each scheme and the compounds of the invention can be isolated or purified according to a conventional method, for example, separating a crude reaction product by cooling, filtrating, concentration, extraction, etc. and then purifying the crude product by chromatography, re-crystallization, etc.

The preferable salt of Compound (1) is a pharmaceutically acceptable salt, and includes, for example, a salt with inorganic base such as metal salt (e.g. an alkali metal salt such as sodium salt and potassium salt, an alkaline earth metal salt such as calcium salt and magnesium salt), ammonium salt, alkali metal carbonate (e.g. lithium carbonate, potassium carbonate, sodium carbonate, cesium carbonate, etc.), alkali metal hydrogen carbonate (e.g. lithium hydrogen carbonate, sodium hydrogen carbonate, potassium hydrogen carbonate, etc.), and alkali metal hydroxide (e.g. lithium hydroxide, sodium hydroxide, potassium hydroxide, cesium hydroxide, etc.);

a salt with organic base such as tri(lower)alkylamine (e.g. trimethylamine, triethylamine, N-ethyl-diisopropylamine, etc.), pyridine, quinoline, piperidine, imidazole, picoline, dimethylaminopyridine, dimethylaniline, N-(lower)alkylmorpholine (e.g. N-methylmorpholine, etc.), DBN, DBU, and DABCO;

a salt of inorganic acid such as hydrochloride, hydrobromide, hydroiodide, sulfate, nitrate, phosphate; and a salt of organic acid such as formate, acetate, propionate, oxalate, malonate, succinate, fumarate, maleate, lactate, malate, citrate, tartrate, carbonate, picrate, methanesulfonate, ethanesulfonate, and p-toluenesulfonate, glutamate.

The starting material used in the above schemes may be a salt thereof like the above Compound (1), and the desired compounds in each reaction may be also appropriate salts.

In addition, solvates of the starting materials and the desired compounds (e.g. hydrate, ethanolate, and the like) are included in each general formula. The preferable solvate includes a hydrate.

The present compounds of the general formula (1) include an isomer such as geometric isomer, stereoisomer, and optical isomer.

The present invention also includes the compound of formula (1) wherein one or more atoms included in the compound are replaced with one or more isotopes thereof. The examples of the isotope which can be incorporated in the present compound include, for example, isotopes of hydrogen, carbon, nitrogen, oxygen, sulfur, fluorine, and chlorine, and in more detail, $^{2}H$, $^{3}H$, $^{13}C$, $^{14}C$, $^{15}N$, $^{17}O$, $^{18}O$, $^{18}F$, $^{36}Cl$, etc. The specific isotope-labeling compound containing the above-mentioned isotope(s) and/or isotope(s) of the other atom(s), for example, the compound including radioisotope(s) such as $^{3}H$ and $^{14}C$, is useful for a topographical assay of the compound and/or the substance. Tritium labeling (i.e. $^{3}H$) or C-14 labeling (i.e. $C^{14}$) isotope compound is especially preferable from the viewpoint of its ease of the preparation and its detectability. Furthermore, the compound which has heavier isotope(s) such as deuterium (i.e. $^{2}H$) is also expected to bring in some therapeutic merits such as the improvement of metabolic stability (e.g. increased in vivo half life) and the reduction of the dosage. The present compounds including isotope atom(s) can be generally prepared by means of the above-mentioned schemes and/or the following examples, using any available isotope labeling reagents.

The compounds of the invention and the salts thereof have an adenosine A2a receptor agonistic activity and thus they are useful as an adenosine A2a receptor agonist for mammals including human beings. Accordingly, the present inventions also provide pharmaceutical compositions as a medicament such as the adenosine A2a receptor agonist.

Hereinafter, the pharmaceutical composition is optionally called as "the present pharmaceutical composition".

The present pharmaceutical composition can be prepared to a usual pharmaceutical formulation comprising an effective amount of at least one compounds selected from the group consisting of the compounds of the invention and the salts thereof, and some pharmaceutically acceptable carriers. The pharmaceutically acceptable carriers used in the pharmaceutical composition of the invention may be a solid such as excipient or a liquid such as diluent. The examples of these carriers include, for example, lactose, magnesium stearate, starch, talc, gelatine, agar, pectin, gum arabic, olive oil, sesame oil, cacao butter, ethylene glycol, purified water, etc.

In addition, the present pharmaceutical composition can be prepared in a formulation of dosage unit suitable for administration. The examples include a solid and liquid formulation suitable for oral administration such as tablet, pill, capsule, granule, powder and liquid as well as a formulation for parenteral administration such as injection (intravenous injection, intramuscular injection, etc.), eye drops, ophthalmic ointment, suppository, percutaneous absorption agent and the like. In particular, the preferable pharmaceutical formulation is eye drops since it is considered that the pharmaceutical composition of the invention can be used as an intraocular pressure reducing agent, a medicine for the treatment of glaucoma and the like, based on the adenosine A2a receptor agonistic activity thereof.

The present pharmaceutical composition can be prepared as an aqueous liquid, and further used as an ophthalmic pharmaceutical composition. For example, such aqueous liquid formulation can be prepared as follows.

To the present compound (including a salt thereof, the same hereinafter) are optionally added one or more additives selected from a pharmaceutically acceptable buffer, isotonic agent, preservative, solubilizer, and pH adjuster, where necessary, and the desired aqueous formulation is prepared via a conventional process.

The buffer used in the aqueous liquid preparation includes, for example, an inorganic acid such as boric acid and phosphoric acid; an organic acid such as an amino acid and succinic acid; and a pharmaceutically acceptable salt. The preferable buffer is succinic acid, phosphoric acid and sodium dihydrogen phosphate. The buffer can be used as a single ingredient or in any combination of two or more ingredients.

The preparation wherein succinic acid or pharmaceutically salt thereof is used as a buffer can prevent the precipitation of the active ingredient during a long-term storage since the salt of the active ingredient with succinic acid has a high solubility.

The concentration of the buffer in the aqueous liquid preparation is preferably a minimum concentration to prevent the pH variation, for example, not more than 2% (w/v), preferably not more than 0.6% (w/v), and more preferably 0.2% (w/v).

The pH adjuster used in the aqueous liquid preparation includes, for example, hydrochloric acid, sulfuric acid, lactic acid, acetic acid, potassium hydroxide, sodium hydroxide, calcium hydroxide, magnesium hydroxide, monoethanolamine, triethanolamine, diisopropanolamine, triisopropanolamine, and a pharmaceutically acceptable salt thereof. The preferable pH adjuster includes hydrochloric acid and sodium hydroxide. The pH adjuster can be used as a single ingredient or in any combination of two or more ingredients.

The isotonic agent used in the aqueous liquid preparation is for making the preparation isotonic to aqueous tear. The isotonic agent herein used is a conventional agent for eye drop, and includes sodium chloride, potassium chloride, boric acid, sodium borate, mannitol, glycerin, propylene glycol, polyethylene glycol, maltose, sucrose, sorbitol, glucose, etc., preferably glycerin, glucose, mannitol, propylene glycol and sorbitol. More preferably, it is glycerin. The isotonic agent can be used as a single ingredient or in any combination of two or more ingredients.

The preparation wherein glycerin is used as an isotonic agent can prevent the deposition of the active ingredient or related substances thereof during a long-term storage since glycerin does not adversely affect the solubility of the active ingredient. The osmotic pressure of the aqueous liquid preparation which includes an isotonic agent is, for example, 170 to 460 mOsm/kg, preferable 229 to 372 mOsm/kg, and more preferable 256 to 316 mOsm/kg.

The preservative herein used includes, for example, a quaternary ammonium salt such as benzalkonium, benzethonium, and benzododecinium; a cation compound such as chlorhexidine; a para-oxybenzoate such as methyl para-oxybenzoate, and propyl para-oxybenzoate; and an alcohol compound such as chlorobutanol and benzylalcohol. The preferable preservative includes benzalkonium chloride and benzododecinium bromide, and more preferably benzalkonium hydrochloride and benzododecinium bromide wherein the alkyl chain is composed of just 12 carbons.

The present pharmaceutical composition may comprise a solubilizer where necessary. The solubilizer herein used includes, for example, a polymer such as polyvinylpyrrolidone, macrogol(polyethylene glycol), polyvinyl alcohol, and hydroxypropylmethylcellulose; a surfactant such as polysorbate, polyoxyethylene hydrogenated castor oil, and polyoxyethylene polyoxypropylene; a polyhydric alcohol such as propylene glycol; an organic acid such as benzoic acid and sorbic acid; an amino acid such as aspartic acid, histidine, glycine, and lysine; and xanthine derivative such as caffeine. The preferable solubilizer includes polyvinylpyrrolidone, macrogol, polyvinyl alcohol, benzoic acid, sorbic acid, and alginic acid; especially polyvinylpyrrolidone and macrogol. The solubilizer can be used as a single ingredient or in any combination of two or more ingredients.

The pH of the aqueous liquid preparation including the present pharmaceutical composition is about 4 to 9, preferably about 5 to 8, especially about 6 to 7, and more preferably 6.3 to 6.9.

The solid formulation of the present invention for oral administration such as tablet, powder and granule can be prepared by mixing the compound of the invention with at least one inert carriers such as lactose, mannitol, glucose, hydroxypropylcellulose, microcrystalline cellulose, starch, polyvinylpyrrolidone, meta-silicic acid and magnesium aluminate, and formulating the mixture according to a conventional method. The preparation may further be formulated with additional appropriate additives, for example, a lubricant such as magnesium stearate; a disintegrator such as calcium cellulose glycolate; a stabilizer such as lactose; a solubilizing agent such as glutamic acid and aspartic acid; and the like. It may further be formulated with a sweetener, a flavor, a perfume, a preservative agent and the like. The tablet and pill may be coated with a sugar-coating film or intragastric- or enteric-coating film, using sucrose, gelatin, hydroxypropylcellulose and hydroxypropylmethylcellulose phthalate, when necessary.

The liquid medicament for oral administration such as emulsion, solution, suspension, syrup and elixir can be prepared by solving or dispersing the compound of the invention in an inert diluent used in general such as purified water and ethanol. The liquid medicament may also contain an auxiliary agent such as wetting agent and suspending agent, a sweetener, flavor, perfume, preservative agent and the like.

The injection for parenteral administration includes aseptic aqueous or nonaqueous solution, suspension, emulsion and the like, and the aqueous injection can be prepared according to a conventional method, for example, using distilled water for injection and saline as a diluent. The nonaqueous injection can be prepared according to a conventional method, for example, using diluent or carrier such as propylene glycol, polyethylene glycol or vegetable oil such as olive oil; alcohols such as ethanol; polysorbate 80. The injection may further contain an auxiliary agent such as a preservative agent, a wetting agent, an emulsifying agent, a dispersing agent, a stabilizer (e.g., lactose) and a solubilizing agent (e.g., glutamic acid and aspartic acid). The injection is sterilized according to a conventional method, for example, by filtration with the filter for removal of bacteria, addition of antimicrobial or radiation such as gamma-ray. In addition, the injection can be also prepared as the extemporaneously preparing formulation, which the prepared aseptic solid medicament is dissolved with aseptic water or aseptic solvent for injection before use.

The dosage regimen for the pharmaceutical composition of the present invention in each the formulation will be determined in each case depending on the condition of the patients to which the pharmaceutical composition is administered (subject for administration), age, sex and so on. In general, the dosage of the eye drops which comprise the pharmaceutical composition of the present invention can be determined to be the amount so that the eye drops containing the active compound in a concentration of 0.0001-10% (w/v), preferably 0.001-1.0% (w/v), more preferably 0.01-0.3% (w/v), can be dropped or swabbed once to several times a day. The amount of the eye drops for one usage is generally about 0.001-1 ml for an adult.

In the case of the oral medicament or the injection of the pharmaceutical composition of the invention, the dosage can be determined so that the compound of the invention can be administered in an amount of 0.001-1000 mg per day in adult. The daily dose may be administered once a day, but preferably be divided in several times. The above dosage is only guideline and hence it may be also increased or decreased. As mentioned above, it is hopeful to determine the dosage every time to be used depending on various conditions. Accordingly, depending on the conditions, the reduced dosage may still exhibit sufficient effects.

Effect of the Invention

The present pharmaceutical compositions and compounds can have as an adenosine A2a receptor agonist various activities such as ocular hypotensive, increased blood flow to optic nerve head, protection of optic nerve, vasodilation, coronary dilatation, fall in blood pressure, platelet aggregation inhibition, antithrombotic effect, antiinflammation, bronchiectasis, and immunosuppression.

Therefore the present pharmaceutical compositions and compounds can be adapted for treating an eye disease such as glaucoma (e.g. normal tension glaucoma, ocular hypertension glaucoma, post-surgical secondary glaucoma, etc.), ocular hypertension, diabetic retinopathy, age-related macular degeneration (ARDM), retinitis pigmentosa (RP), and retinal disease caused by glaucoma; hypertension; congestive heart failure; coronary ailment; angina; atherosclerosis; ischemic heart disease; cerebrovascular ischemia; reperfusion injury; thrombosis; epilepsy; rhinitis; sinusitis; emphysema; chronic obstructive pulmonary disease (COPD); asthma; bronchitis; respiratory disease; respiratory insufficiency syndrome; septic shock; pulmonary fibrosis; gastritis; metastasis gastritis; ulcerative colitis; Crohn's disease; inflammatory colonic disease; wound healing; eczema; cutaneous hypersensitivity; dermatitis; psoriasis; chronic rheumatoid arthritis; diabetes; multiple sclerosis; autoimmune disease; etc.

In addition, the present pharmaceutical compositions and compounds can be used as a diagnostic agent for myocardial infarction.

Hereinafter, the present invention is illustrated by Reference Examples for preparing the starting compounds and by Example for preparing the compounds and formulations of the invention, and also experiments of the pharmacological tests, but should not be construed to be limited thereto.

The nuclear magnetic resonance (NMR) spectra in the examples mentioned below were measured under the following conditions. The abbreviate symbols are defined as follows.

Apparatus: JNM-AL300 (JEOL)
Internal standard substance: TMS
s: singlet, d: doublet, t: triplet, q: quartet, quint: quintet, sext: sextet

BEST MODE FOR CARRYING OUT THE INVENTION

Reference Example 1

Methyl(E)-3-(6-hydroxymethylpyridin-2-yl)acrylate

Figure 1:
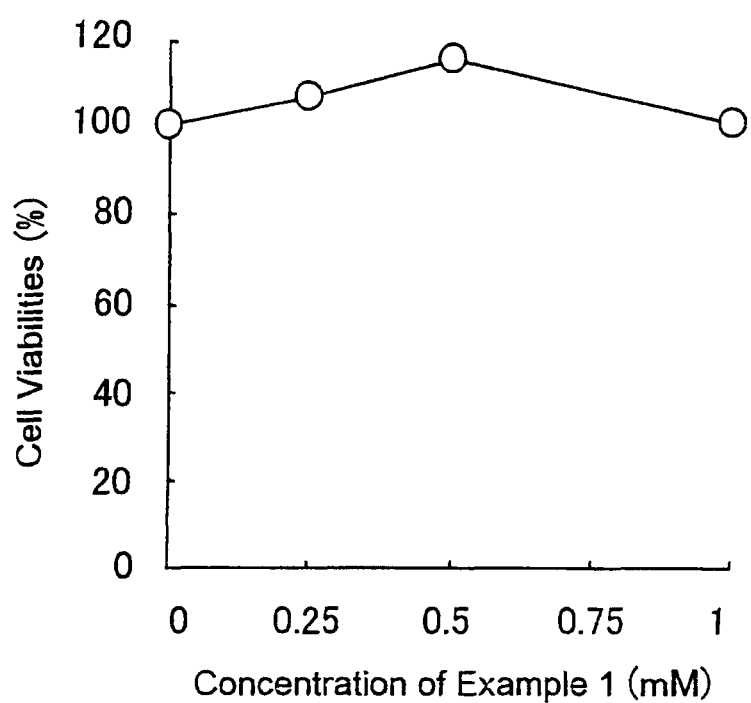
FIG. 1 shows the cell viabilities that the compound of Example 1 in 0.25, 0.5 and 1 mM was added to rabbit corneal epithelium cells.

2-Bromopyridine-6-methanol (50.0 g) was dissolved in dry N,N-dimethylformamide (250 ml). To the solution were added methyl acrylate (47.9 ml), tetra(n-butyl)ammonium chloride (73.9 g), sodium hydrogen carbonate (47.7 g) and Molecular Sieves 3A(1/16) (50.0 g), and further palladium(II) acetate (2.98 g) was added thereto under argon atmosphere. The mixture was stirred at 80° C. for 5 hours. After cooling the reaction mixture, the resulting precipitate was filtered off, and water was added to the filtrate, which was extracted with ethyl acetate. The organic layer was washed with brine, dried over anhydrous magnesium sulfate and concentrated in vacuo to give 50.2 g of methyl(E)-3-(6-hydroxymethylpyridin-2-yl)acrylate.

Brown Powder.

$^1$H-NMR (CDCl$_3$) 7.72 (1H, t, J=7.5 Hz), 7.68 (1H, d, J=15.6 Hz), 7.32 (1H, d, J=7.5 Hz), 7.21 (1H, d, J=7.5 Hz), 6.97 (1H, d, J=15.6 Hz), 4.78 (2H, d, J=4.2 Hz), 3.85 (1H, t, J=4.2 Hz), 3.83 (3H, s).

Reference Example 2

Methyl 3-(6-hydroxymethylpyridin-2-yl)propionate

Methyl(E)-3-(6-hydroxymethylpyridin-2-yl)acrylate (50.2 g) was almost dissolved in isopropyl alcohol (502 ml). To the solution was added 5% palladium-(activated carbon) (2.51 g), and the mixture was stirred at 50° C. under normal pressured hydrogen atmosphere for 2.5 hours. After cooling the reaction mixture, the catalyst was filtered off and the filtrate was concentrated in vacuo to give 50.0 g of methyl 3-(6-hydroxymethylpyridin-2-yl)propionate.
Brown Oil.

$^1$H-NMR (CDCl$_3$) 7.58 (1H, t, J=7.5 Hz), 7.09 (1H, d, J=7.5 Hz), 7.03 (1H, d, J=7.5 Hz), 4.71 (2H, s), 4.01 (1H, br s), 3.69 (3H, s), 3.15 (2H, t, J=7.2 Hz), 2.81 (2H, t, J=7.2 Hz).

Reference Example 3

Methyl 3-(6-methanesulfonyloxymethylpyridin-2-yl)propionate

Methyl 3-(6-hydroxymethylpyridin-2-yl)propionate (50.0 g) was dissolved in ethyl acetate (1000 ml). To the solution was added triethylamine (53.5 ml), and the mixture was stirred at ice temperature for 10 minutes. To the mixture was added methanesulfonyl chloride (23.8 ml) dropwise over 10 minutes, and the resulting mixture was stirred at ice temperature for 30 minutes. To the reaction mixture was added water, and the mixture was transferred into a separating funnel, and washed with aqueous saturated sodium hydrogen carbonate and brine, dried over anhydrous magnesium sulfate and concentrated in vacuo to give 63.0 g of methyl 3-(6-methanesulfonyloxymethylpyridin-2-yl)propionate.
Brown Oil.

$^1$H-NMR (CDCl$_3$) 7.63 (1H, t, J=7.5 Hz), 7.26 (1H, d, J=7.5 Hz), 7.19 (1H, d, J=7.5 Hz), 5.28 (2H, s), 3.67 (3H, s), 3.12 (2H, t, J=7.2 Hz), 3.07 (3H, S), 2.79 (2H, t, J=7.2 Hz).

Reference Example 4

Methyl 3-{6-[4-(4-acetylaminophenyl)-6-amino-5-cyanopyrimidin-2-ylthiomethyl]pyridin-2-yl}propionate 4-Acetamide-benzaldehyde (1000 g) was dissolved in ethanol (16000 ml). To the mixture were added malononitrile (607 g) and piperidine (40 g), and the resulting mixture was stirred under reflux for 2 hours. The reaction mixture was cooled to room temperature and then stirred for 30 minutes. The precipitated crystal was collected on a filter, washed with ethanol (2000 ml) and dried to give 1049 g of N-[4-(2,2-dicyanovinyl)phenyl]acetamide as a yellow powder.

Methyl 3-(6-methanesulfonyloxymethylpyridin-2-yl)propionate (7.0 g) was dissolved in methanol (75 ml), and then thiourea (1.85 g) was added thereto. The mixture was refluxed for 1.5 hours. After cooling the reaction mixture, triethylamine (10.7 ml) was added thereto, and the mixture was stirred for a while. Subsequently, methanol (75 ml), the above N-[4-(2,2-dicyanovinyl)phenyl]acetamide (4.33 g), and then N-bromosuccinimide (3.67 g) were added thereto, and the mixture was stirred for 1 hour. The precipitated crystal was collected on a filter, washed with methanol (40 ml), and dried to give 5.5 g of methyl 3-{6-[4-(4-acetylaminophenyl)-6-amino-5-cyanopyrimidin-2-ylthiomethyl]pyridin-2-yl}propionate.
White Powder.

$^1$H-NMR (DMSO-d$_6$) 10.23 (1H, s), 8.20-7.60 (2H, br s), 7.83 (2H, d, J=8.7 Hz), 7.72 (2H, d, J=8.7 Hz), 7.63 (1H, t, J=7.8 Hz), 7.35 (1H, d, J=7.8 Hz), 7.15 (1H, d, J=7.8 Hz), 4.45 (2H, s), 3.57 (3H, s), 2.96 (2H, t, J=7.2 Hz), 2.74 (2H, t, J=7.2 Hz), 2.09 (3H, s).

Reference Example 5

3-{6-[4-(4-Acetylaminophenyl)-6-amino-5-cyanopyrimidin-2-ylthiomethyl]pyridin-2-yl}propionic acid Methyl 3-{6-[4-(4-acetylaminophenyl)-6-amino-5-cyanopyrimidin-2-ylthiomethyl]pyridin-2-yl}propionate (5 g) was suspended in 50% water-containing acetonitrile (150 ml). To the suspension was added lithium hydroxide monohydrate (1.35 g), and the mixture was stirred at room temperature for 1 hour. Then a solution of citric acid (4.11 g) in water (20 ml) was gradually added to the reaction mixture, and the reaction mixture was stirred at room temperature for additional 2 hours. The precipitated crystal was collected on a filter, washed with water (75 m), and dried to give 5 g of 3-{6-[4-(4-acetylaminophenyl)-6-amino-5-cyanopyrimidin-2-ylthiomethyl]pyridin-2-yl}propionic acid.
White Powder.

$^1$H-NMR (DMSO-d$_6$) 10.25 (1H, s), 7.84 (2H, d, J=8.7 Hz), 7.72 (2H, d, J=8.7 Hz), 7.64 (1H, t, J=7.8 Hz), 7.36 (1H, d, J=7.8 Hz), 7.16 (1H, d, J=7.8 Hz), 4.47 (2H, s), 2.95 (2H, t, J=7.2 Hz), 2.65 (2H, t, J=7.2 Hz), 2.09 (3H, s).

Reference Example 6

1-tert-Butoxycarbonyl-4-(piperazin-1-yl)methylpiperidine 1-tert-Butoxycarbonyl-4-piperidylmethanol (10 g) was dissolved in ethyl acetate (150 ml). To the solution was added triethylamine (12.8 ml), and the mixture was stirred at ice temperature for a while. To the mixture was slowly added methanesulfonyl chloride (5.4 ml) dropwise, and the reaction mixture was stirred at ice temperature for 30 minutes. To the reaction mixture was added water, and the mixture was transferred into a separating funnel, washed with water (50 ml), and extracted with ethyl acetate (50 ml, twice). The combined organic layer was dried over anhydrous magnesium sulfate and concentrated in vacuo. The residue was dissolved in acetonitrile (200 ml), and piperazine (18 g) was added to the solution. The mixture was stirred under reflux for 3 hours. The reaction mixture was concentrated in vacuo, then the precipitated piperazine was filtrated off. To the filtrate were added brine (50 ml) and ethyl acetate (50 ml), and the mixture was stirred overnight. The mixture was transferred into a separating funnel, and the organic layer was separated, washed with brine (50 ml, twice), and concentrated in vacuo. To the residue was added water (50 ml), and the mixture was neutralized with 1N hydrochloric acid at ice temperature. Ethyl acetate (100 ml) was added thereto and the mixture was stirred for a while. Then the mixture was transferred into a separating funnel, and the aqueous layer was separated. The aqueous layer was strongly basified with 5N sodium hydroxide at ice temperature. The mixture was extracted with ethyl acetate, dried over anhydrous magnesium sulfate and concentrated in vacuo to give 9.96 g of 1-tert-butoxycarbonyl-4-(piperazin-1-yl)methylpiperidine.
Colorless Oil.
$^1$H-NMR (CDCl$_3$) 4.11-4.05 (2H, m), 2.87 (4H, t, J=4.8 Hz), 2.72-2.64 (2H, m), 2.36 (4H, br s), 2.14 (2H, d, J=6.9 Hz), 1.74-1.65 (3H, m), 1.45 (9H, m), 1.13-0.99 (2H, m).

Reference Example 7

4-((4-(3-(6-((4-(4-Acetamidophenyl)-6-amino-5-cyanopyrimidin-2-ylthio)methyl)pyridin-2-yl)propanoyl)piperazin-1-yl)methyl)-1-tert-butoxycarbonylpiperidine dihydrochloride 3-{6-[4-(4-Acetylaminophenyl)-6-amino-5-cyanopyrimidin-2-ylthiomethyl]pyridin-2-yl}propionic acid (2.16 g) was suspended in acetone (44 ml). To the suspension were added 1-hydroxy-1H-benzotriazole (781 mg), 1-ethyl-3-(3-dimethylaminopropyl)-carbodiimide hydrochloride (1.1 g), and 1-tert-butoxycarbonyl-4-(piperazin-1-yl)methylpiperidine (1.5 g) in order, and the mixture was refluxed for 1 hour. The acetone was removed off in vacuo, and then ethyl acetate (30 ml) and water (30 ml) were added thereto, and the mixture was stirred for 30 minutes. The mixture was transferred into a separating funnel, washed with saturated aqueous sodium hydrogen carbonate and brine in order, dried over anhydrous magnesium sulfate and concentrated in vacuo. The residue was completely dissolved in methanol (25 ml), then conc. hydrochloric acid (0.85 ml) was slowly added thereto dropwise at ice temperature, and the mixture was stirred at room temperature for 1 hour. Then, ethanol (50 ml) was added thereto, and the mixture was stirred at 50° C. for 1 hour. After cooling the reaction mixture, the precipitated crystal was collected on a filter, and dried to give 2.95 g of 4-((4-(3-(6-((4-(4-acetamidophenyl)-6-amino-5-cyanopyrimidin-2-ylthio)methyl)pyridin-2-yl)propanoyl)piperazin-1-yl)methyl)-1-tert-butoxycarbonylpiperidine dihydrochloride.
White Powder.
$^1$H-NMR (DMSO-d$_6$) 10.30 (1H, s) 10.15 (1H, br-s) 8.00-7.81 (4H, m) 7.72 (2H, d, J=8.7 Hz) 7.65 (1H, br-s) 7.40 (1H, br-s) 4.57 (2H, s) 4.36-4.31 (1H, m) 4.02-3.89 (3H, m) 3.70-3.30 (8H, m) 3.17-2.73 (8H, m) 2.09 (3H, s) 1.99 (1H, m) 1.78-1.73 (2H, m) 1.39 (9H, s).

Example 1

N-(4-(6-amino-5-cyano-2-((6-(3-oxo-3-(4-(piperidin-4-yl-methyl)piperazin-1-yl)propyl)pyridin-2-yl)methylthio)-pyrimidin-4-yl)phenyl)acetamide trihydrochloride To 4-((4-(3-(6-((4-(4-acetamidephenyl)-6-amino-5-cyanopyrimidin-2-ylthio)methyl)pyridin-2-yl)propanoyl)-piperazin-1-yl)methyl)-1-tert-butoxycarbonylpiperidine dihydrochloride (40 g) was added 400 ml of hydrogen chloride [1 mol/L in ethyl acetate], and the mixture was stirred at room temperature for 24 hours. The precipitate was collected on a filter and washed with ethyl acetate (80 ml). The precipitate was dried to give a white crude crystal. The crude crystal was dissolved in water (245 ml) at room temperature, and filtrated. To the filtrate was slowly added acetone (875 ml), and the mixture was stirred with a seed crystal thereof for 6 hours. The precipitated crystal was collected on a filter, washed with acetone (140 ml), and then dried to give 29.8 g of N-(4-(6-amino-5-cyano-2-((6-(3-oxo-3-(4-(piperidin-4-ylmethyl)piperazin-1-yl)propyl)pyridin-2-yl)methylthio)pyrimidin-4-yl)phenyl)-acetamide trihydrochloride.
White Powder.
$^1$H-NMR (DMSO-d$_6$) 11.23 (1H, br-s) 10.43 (1H, s) 9.05 (1H, br-s) 8.93 (1H, br-s) 8.30 (1H, t, J=7.8 Hz) 7.96 (1H, d, J=7.8 Hz) 7.81 (2H, d, J=8.7 Hz) 7.78-7.73 (3H, m) 4.77 (2H, s) 4.36-4.31 (1H, m) 4.02-3.74 (3H, m) 3.53-3.45 (2H, m) 3.26-3.23 (5H, m) 3.02-2.81 (8H, m) 2.10-1.91 (6H, m) 1.50-1.39 (2H, m).

Example 2

N-(4-(6-amino-5-cyano-2-((6-(3-(4-((1-(2-hydroxyethyl)-piperidin-4-yl)methyl)piperazin-1-yl)-3-oxopropyl)pyridin-2-yl)methylthio)pyrimidin-4-yl)phenyl)acetamide maleate N-(4-(6-Amino-5-cyano-2-((6-(3-oxo-3-(4-(piperidin-4-ylmethyl)piperazin-1-yl)propyl)pyridin-2-yl)methylthio)-pyrimidin-4-yl)phenyl)acetamide trihydrochloride (1.01 g) was dissolved in dry N,N-dimethylformamide (15 ml). To the solution were added 2-chloroethanol (186 μl), triethylamine (0.6 ml), potassium carbonate (386 mg), and sodium iodide (300 mg), and the mixture was stirred at 50° C. for 3 hours. The reaction mixture was concentrated under reduced pressure, and the residue was purified by chromatography on silica gel (methylene chloride:methanol:28% aqueous ammonia=100:10:1) to give 220 mg of N-(4-(6-amino-5-cyano-2-((6-(3-(4-((1-(2-hydroxyethyl)piperidin-4-yl)-methyl)piperazin-1-yl)-3-oxopropyl)pyridin-2-yl)methylthio)pyrimidin-4-yl)phenyl)acetamide. The compound was dissolved in methanol (5 ml), and maleic acid (38.8 mg) was added thereto. The mixture was stirred for a while. The solution was concentrated in vacuo to give 250 mg of N-(4-(6-amino-5-cyano-2-((6-(3-(4-((1-(2-hydroxyethyl)piperidin-4-yl)methyl)piperazin-1-yl)-3-oxopropyl)pyridin-2-yl)-methylthio)pyrimidin-4-yl)phenyl)acetamide maleate.
White Powder.
$^1$H-NMR (DMSO-d$_6$) 10.25 (1H, s) 7.83 (2H, d, J=8.7 Hz) 7.71 (2H, d, J=8.7 Hz) 7.63 (1H, t, J=7.5 Hz) 7.35 (1H, d, J=7.5 Hz) 7.15 (1H, d, J=7.5 Hz), 6.04 (2H, s) 5.76 (1H, br-s) 4.47-4.35 (4H, m) 3.71 (2H, br-s) 3.45-3.32 (9H, m) 3.11 (2H, br-s) 2.97-2.87 (4H, m) 2.73-2.69 (2H, m) 2.36-2.19 (3H, m) 2.09 (3H, s) 1.88-1.83 (3H, m) 1.35-1.31 (2H, m).

The following examples 3-5 were prepared according to a similar process to Example 2.

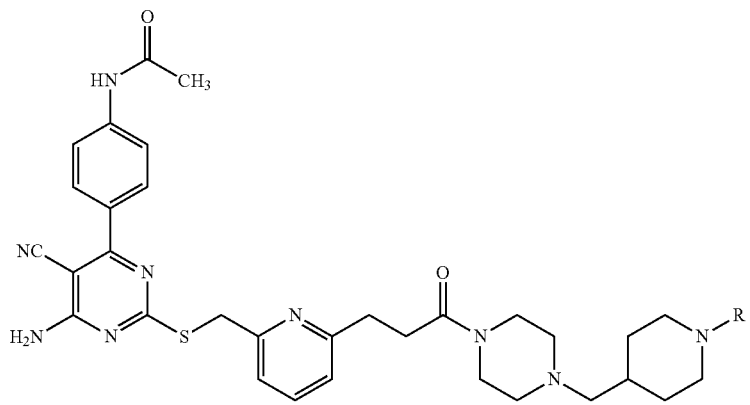

| Example | R | NMR data | Salt |
|---|---|---|---|
| 1 | H | 1H-NMR (DMSO-d6) 11.23 (1H, br-s) 10.43 (1H, s) 9.05 (1H, br-s) 8.93 (1H, br-s) 8.30 (1H, t, J = 7.8 Hz) 7.96 (1H, d, J = 7.8 Hz) 7.81 (2H, d, J = 8.7 Hz) 7.78-7.73 (3H, m) 4.77 (2H, s) 4.36-4.31 (1H, m) 4.02-3.74 (3H, m) 3.53-3.45 (2H, m) 3.26-3.23 (5H, m) 3.02-2.81 (8H, m) 2.10-1.91 (6H, m) 1.50-1.39 (2H, m). | trihydrochloride |
| 2 | ~~~OH | DMSOd-6: 10.25 (1H, s) 7.83 (2H, d, J = 8.7 Hz) 7.71 (2H, d, J = 8.7 Hz) 7.63 (1H, t, J = 7.5 Hz) 7.35 (1H, d, J = 7.5 Hz) 7.15 (1H, d, J = 7.5 Hz), 6.04 (2H, s) 5.76 (1H, br-s) 4.47-4.35 (4H, m) 3.71 (2H, br-s) 3.45-3.32 (9H, m) 3.11 (2H, br-s) 2.97-2.87 (4H, m) 2.73-2.69 (2H, m) 2.36-2.19 (3H, m) 2.09 (3H, s) 1.88-1.83 (3H, m) 1.35-1.31 (2H, m) | maleate |
| 3 | ~~~~OH | DMSOd-6: 10.25 (1H, s) 7.83 (2H, d, J = 8.7 Hz) 7.72 (2H, d, J = 8.7 Hz) 7.62 (1H, t, J = 7.8 Hz) 7.34 (1H, d, J = 7.8 Hz) 7.14 (1H, d, J = 7.8 Hz), 4.46 (2H, s) 3.44-3.29 (8H, m) 2.94 (2H, t, J = 7.5 Hz) 2.87-2.83 (2H, m) 2.73-2.66 (2H, m) 2.34 (2H, br-s) 2.20-2.18 (4H, m) 2.09 (3H, s) 2.03 (2H, d, J = 7.2 Hz) 1.87 (2H, br-s) 1.64-1.43 (4H, m), 1.09-1.01 (2H, m) | |
| 4 | ~~~F | CDCl3: 7.99 (2H, d, J = 8.7 Hz) 7.75-7.60 (2H, m) 7.51 (1H, t, J = 7.5 Hz) 7.27 (1H, d, J = 7.5 Hz) 7.07 (1H, d, J = 7.5 Hz), 5.85 (br-s, 2H) 4.65 (1H, t, J = 5.1 Hz) 4.53-4.42 (1H, m) 4.49 (2H, s) 3.59 (1H, t, J = 4.8 Hz) 3.53-3.40 (2H, m) 3.13 (2H, t, J = 6.9 Hz) 3.00-2.90 (2H, m) 2.80 (2H, t, J = 6.9 Hz) 2.73 (1H, t, J = 4.8 Hz) 2.63 (2H, t, J = 4.8 Hz) 2.38-2.25 (4H, m) 2.21 (3H, s) 2.14 (2H, d, J = 7.5 Hz) 2.10-1.97 (2H, m) 1.85-1.60 (2H, m) 1.55-1.40 (1H, m) 1.35-1.15 (2H, m) | |

-continued
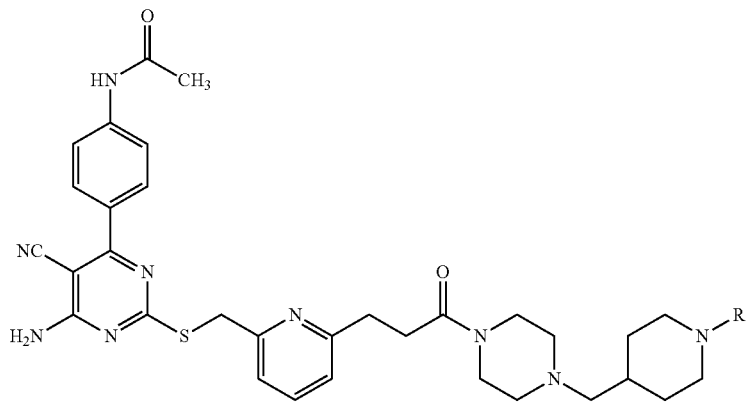
| Example | R | NMR data | Salt |
|---|---|---|---|
| 5 | ![structure](methyl butanoate group) | DMSOd-6: 10.25 (1H, s) 7.84 (2H, d, J = 8.7 Hz) 7.72 (2H, d, J = 8.7 Hz) 7.62 (1H, t, J = 7.8, Hz) 7.34 (1H, d, J = 7.8 Hz) 7.14 (1H, d, J = 7.8 Hz) 4.46 (2H, s) 3.59 (3H, s) 3.50-3.25 (4H, m) 2.98-2.76 (3H, m) 2.75-2.50 (3H, m) 2.50-2.40 (4H, m) 2.25-2.13 (4H, m) 2.09 (3H, s) 2.04 (2H, d, J = 7.2 Hz), 1.68-1.55 (2H, m) 1.50-1.35 (1H, m) 1.15-0.98 (2H, m) | |
Example 6
N-(4-(6-amino-5-cyano-2-(6-(3-oxo-3-(4-(piperidin-4-yl-methyl)piperazin-1-yl)propyl)pyridin-2-yl)methylthio)-pyrimidin-4-yl)phenyl)acet-D3-amide trihydrochloride (6-3)
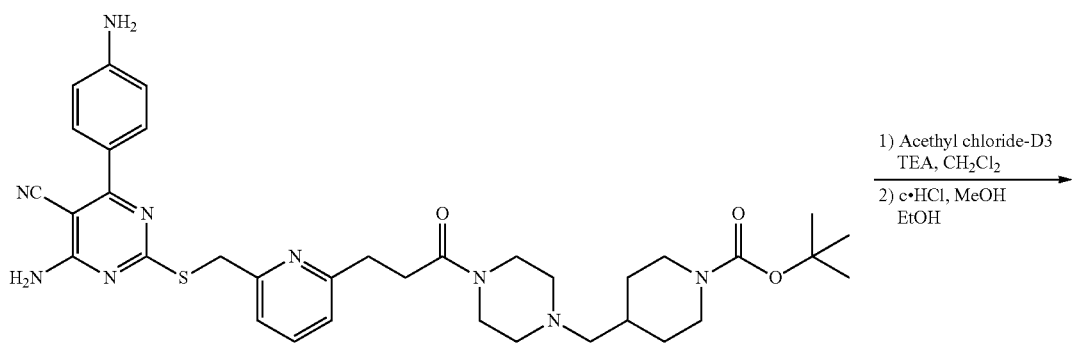
1) Acethyl chloride-D3
   TEA, CH$_2$Cl$_2$
2) c•HCl, MeOH
   EtOH
6-1

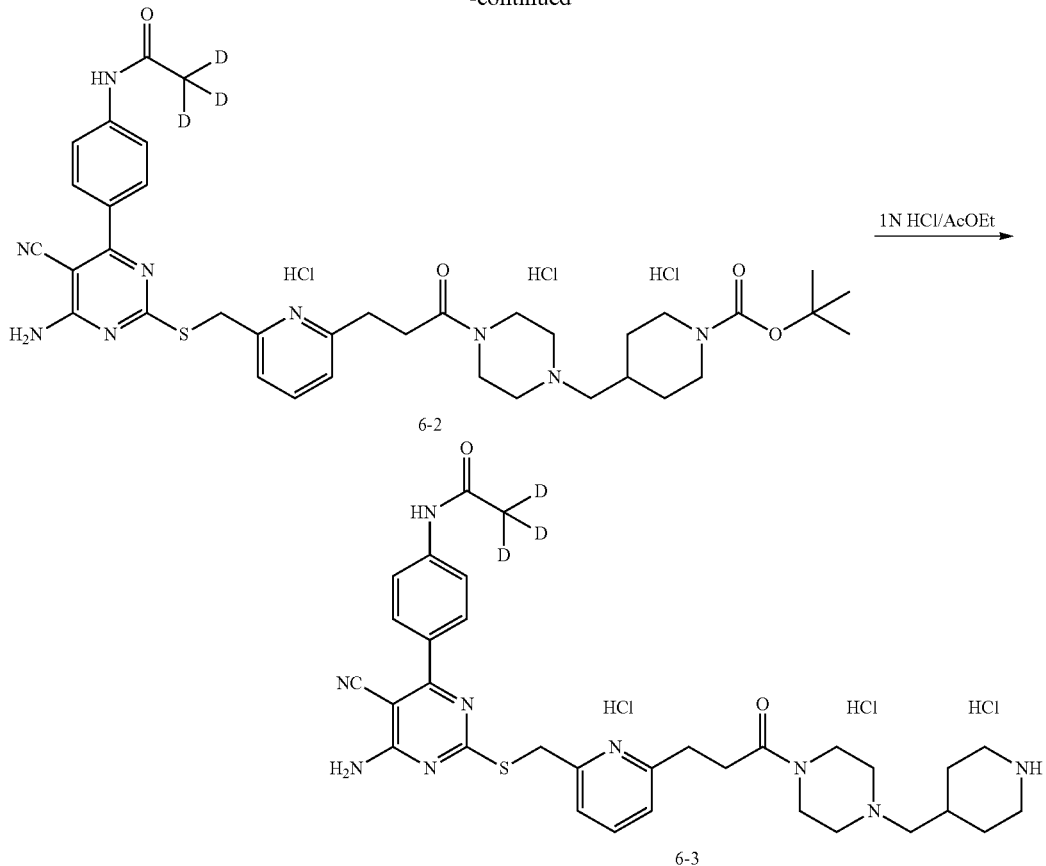

t-Butyl 4-(4-(3-(6-(4-(4-acet-D3-amidophenyl)-6-amino-5-cyanopyrimidin-2-ylthio)methyl)pyridin-2-yl)-propanoyl)piperazin-1-yl)methyl)piperidine-1-carboxylate dihydrochloride (6-2)

t-Butyl 4-(4-(3-(6-((4-amino-6-(4-aminophenyl)-5-cyanopyrimidin-2-ylthio)methyl)pyridin-2-yl)propanoyl)-piperazin-1-yl)methyl)piperidine-1-carboxylate (6-1) (3.4 g) was dissolved in methylene chloride (68 ml). To the solution was added triethylamine (1.4 ml) at ice temperature, and the mixture was stirred for a while. Acetyl-D3 chloride (532 μl) was slowly added thereto dropwise, and the mixture was stirred at room temperature overnight. Water was added thereto and the mixture was transferred into a separating funnel. The aqueous layer was extracted with methylene chloride (twice), and the combined organic layer was dried over anhydrous magnesium sulfate and concentrated in vacuo. The residue was purified by chromatography on silica gel (methylene chloride:methanol=25:1) to give 3.1 g of t-butyl 4-(4-(3-(6-(4-(4-acet-D3-amidophenyl)-6-amino-5-cyanopyrimidin-2-ylthio)methyl)pyridin-2-yl)propanoyl) piperazin-1-yl)methyl)piperidine-1-carboxylate. The compound was completely dissolved in methanol (20 ml), then conc. HCl (1.7 ml) was slowly added thereto dropwise at ice temperature, and the mixture was stirred at room temperature for 3 hours. Then, ethanol (40 ml) was added thereto and the mixture was stirred at 50° C. for 1 hour. After cooling the reaction mixture, the precipitated crystal was collected on a filter, and dried to give 2.06 g of t-butyl 4-((4-(3-(6-((4-(4-acet-D3-amidophenyl)-6-amino-5-cyanopyrimidin-2-yl-thio)methyl)pyridin-2-yl)propanoyl)-piperazin-1-yl)methyl) piperidine-1-carboxylate dihydrochloride (6-2).

White Powder.

$^1$H-NMR (DMSO-$d_6$) 10.29 (1H, s) 10.15 (1H, br-s) 8.00-7.90 (1H, m) 7.82 (2H, d, J=8.7 Hz) 7.73 (2H, d, J=8.7 Hz) 7.59 (1H, m) 7.40 (1H, m) 4.57 (2H, s) 4.36-4.31 (1H, m) 4.02-3.89 (3H, m) 3.70-3.30 (8H, m) 3.17-2.73 (8H, m) 1.99 (1H, m) 1.78-1.73 (2H, m) 1.39 (9H, s).

N-(4-(6-Amino-5-cyano-2-(6-(3-oxo-3-(4-(piperidin-4-ylmethyl)piperazin-1-yl)propyl)pyridin-2-yl)meth-ylthio)-pyrimidin-4-yl)phenyl)acet-D3-amide trihydrochloride (6-3)

To t-butyl 4-(4-(3-(6-(4-(4-acet-D3-amidophenyl)-6-amino-5-cyanopyrimidin-2-ylthio)methyl)pyridin-2-yl)-propanoyl)piperazin-1-yl)methyl)piperidine-1-carboxylate dihydrochloride (6-2) (2.0 g) was added 20 ml of hydrogen chloride [1 mol/L in ethyl acetate], and the mixture was stirred at room temperature for 41 hours. The precipitate was collected on a filter and washed with ethyl acetate (4.0 ml). The crude crystal was dissolved in water (10 ml) at room temperature, and filtrated. To the filtrate was slowly added acetone (40 ml), and the mixture was stirred with a seed crystal thereof for 2 hours. The precipitated crystal was collected on a filter, washed with acetone (4 ml), and then dried to give 1.75 g of N-(4-(6-amino-5-cyano-2-(6-(3-oxo-3-(4-(piperidin-4-ylmethyl)piperazin-1-yl)propyl)pyridin-2-yl)methylthio)pyrimidin-4-yl)phenyl)-acet-D3-amide trihydrochloride (6-3).

White Powder.
¹H-NMR (DMSO-d₆) 11.06 (1H, br-s) 10.38 (1H, s) 8.94-8.81 (2H, m) 8.16 (1H, t, J=7.8 Hz) 7.83-7.80 (3H, m) 7.75 (2H, d, J=8.7 Hz) 7.64 (1H, d, J=7.8 Hz) 4.70 (2H, s) 4.36-4.31 (1H, m) 4.02-3.74 (3H, m) 3.53-3.45 (2H, m) 3.26-3.23 (5H, m) 3.02-2.81 (8H, m) 2.10-1.91 (3H, m) 1.50-1.39 (2H, m).
Example 7
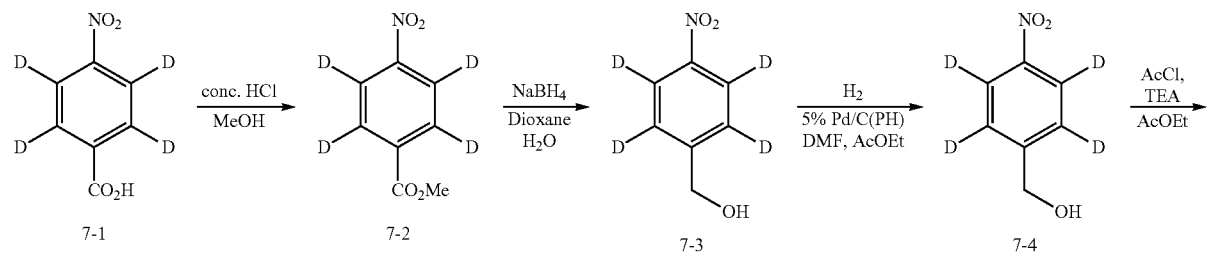
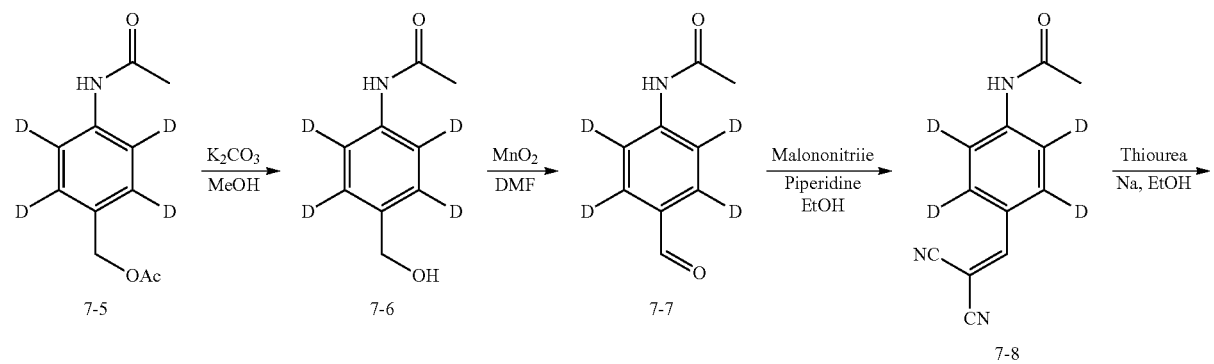
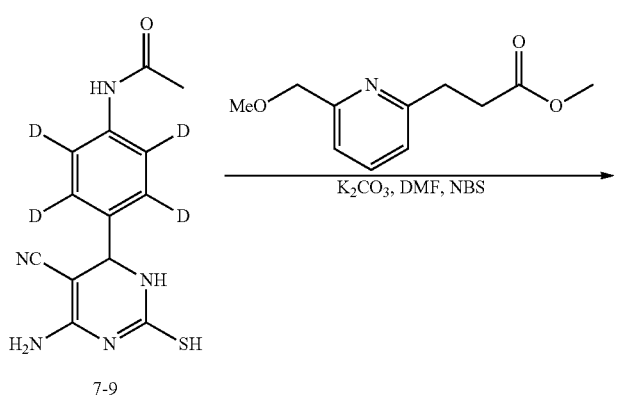
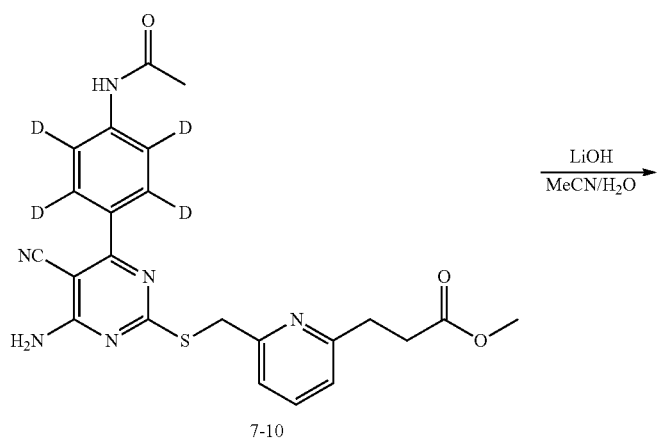

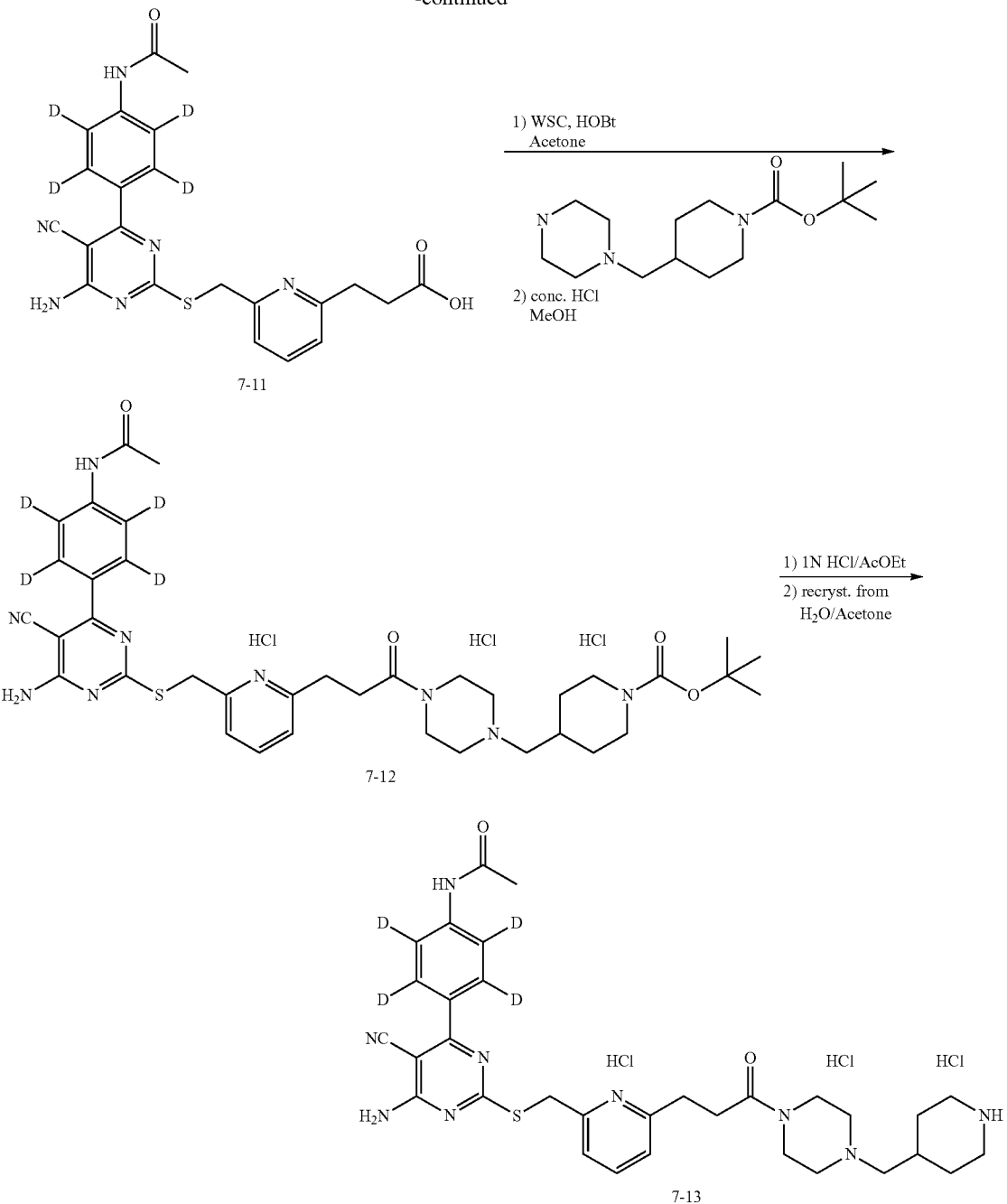

Methyl 4-nitrobenzoate-2,3,5,6-D4 (7-2)

4-Nitrobenzoic-D4 acid (7-1) (5 g) was dissolved in methanol (100 ml). To the solution was added conc. hydrochloric acid (1.0 ml), and the mixture was refluxed for 15 hours. The reaction mixture was concentrated in vacuo and then water was added to the residue. The mixture was extracted with methylene chloride. The organic layer was washed with aqueous sodium hydrogen carbonate, dried over anhydrous magnesium sulfate, and concentrated in vacuo to give 5.3 g of methyl 4-nitrobenzoate-2,3,5,6-D4 (7-2).

White Powder.
$^1$H-NMR (CDCl$_3$) 3.99 (3H, s).

4-Nitrobenzyl-2,3,5,6-D4 alcohol (7-3)

Methyl 4-nitrobenzoate-2,3,5,6-D4 (7-2) (5.3 g) was suspended in a mixture of dioxane (53 ml) and water (53 ml). To the suspension was added sodium borohydride (9.4 g), and the mixture was stirred at room temperature for 6 hours. After the reaction was completed, the reaction mixture was weakly acidified with 5 N HCl and transferred into a separating funnel. The aqueous layer was extracted with ethyl acetate and the combined organic layer was dried over anhydrous magnesium sulfate and concentrated in vacuo to give 3.75 g of 4-nitrobenzyl-2,3,5,6-D4 alcohol (7-3).
Yellow Powder.
$^1$H-NMR (DMSO-$d_6$) 5.53 (1H, t, J=5.7 Hz) 4.64 (2H, d, J=5.7 Hz).

4-Aminobenzyl-2,3,5,6-D4 alcohol (7-4)

4-Nitrobenzyl-2,3,5,6-D4 alcohol (7-3) (3.75 g) was dissolved in a mixture of ethyl acetate (37 ml) and dimethylformamide (10 ml). To the solution was added 5% palladium-(activated carbon) (400 mg), and the mixture was stirred under atmospheric hydrogen pressure for 6 hours. After the reaction was completed, the catalyst was filtered off and the filtrate was concentrated in vacuo to give 2.65 g of 4-aminobenzyl-2,3,5,6-D4 alcohol (7-4).
Yellow Oil.
$^1$H-NMR (CDCl$_3$) 4.56 (2H, s).

4-Acetamidobenzyl-2,3,5,6-D4 acetate (7-5)

4-Aminobenzyl-2,3,5,6-D4 alcohol (7-4) (2.65 g) was dissolved in ethyl acetate (53 ml). To the solution was added triethylamine (12.9 ml) at ice temperature, and the mixture was stirred for a while. And then acetyl chloride (5.5 ml) was slowly added thereto dropwise, and the mixture was stirred for 1 hour. After the reaction was completed, water was added to the reaction mixture, and the mixture was transferred into a separating funnel. The aqueous layer was extracted with ethyl acetate and the combined organic layer was dried over anhydrous magnesium sulfate and concentrated in vacuo to give 4.28 g of 4-acetamidobenzyl-2,3,5, 6-D4 acetate (7-5).
Yellow Oil.
$^1$H-NMR (DMSO-$d_6$) 4.99 (2H, s) 2.09 (6H, s).

N-(4-(Hydroxymethyl)phenyl-2,3,5,6-D4)acetamide (7-6)

4-Acetamidebenzyl-2,3,5,6-D4 acetate (7-5) (4.28 g) was dissolved in methanol (80 ml). To the solution was added potassium carbonate (2.9 g), and the mixture was stirred for 1.5 hours. After the reaction was completed, the reaction mixture was filtrated. The filtrate was concentrated in vacuo to give 3.4 g of N-(4-(hydroxymethyl)phenyl-2,3,5,6-D4) acetamide (7-6).
Yellow Oil.
$^1$H-NMR (DMSO-$d_6$) 10.07 (1H, s) 4.42 (2H, s) 2.02 (3H, s).

N-(4-Formylphenyl-2,3,5,6-D4)acetamide (7-7)

N-(4-(Hydroxymethyl)phenyl-2,3,5,6-D4)acetamide (7-6) (3.4 g) was dissolved in dimethylformamide (68 ml). To the solution was added manganese dioxide (17 g), and the mixture was stirred at 60° C. for 6 hours. After the reaction was completed, the reaction mixture was filtrated. To the filtrate was added water, and the mixture was extracted with ethyl acetate. The organic layer was dried over anhydrous magnesium sulfate and concentrated in vacuo to give 2.5 g of N-(4-formylphenyl-2,3,5,6-D4)acetamide (7-7).
White Powder.
$^1$H-NMR (CDCl$_3$) 9.93 (1H, s) 7.50 (1H, br-s) 2.23 (3H, m).

N-(4-(2,2-Dicyanovinyl)phenyl-2,3,5,6-D4)acetamide (7-8)

N-(4-Formylphenyl-2,3,5,6-D4)acetamide (7-7) (2.5 g) was dissolved in ethanol (50 ml). To the solution were added malononitrile (1.1 g) and piperidine (2 drops), and the mixture was stirred at room temperature for 8 hours. The precipitated crystal was collected on a filter, washed with ethanol, and dried to give 2.1 g of N-(4-(2,2-dicyanovinyl) phenyl-2,3,5,6-D4)acetamide (7-8).
Yellow Powder.
$^1$H-NMR (DMSO-$d_6$) 10.52 (1H, s) 8.37 (1H, s) 2.12 (3H, s).

N-(4-(6-Amino-5-cyano-2-mercapto-3,4-dihydropyrimidin-4-yl)phenyl-2,3,5,6-D4)acetamide (7-9)

To 20 ml of an ethanol solution wherein metal sodium (276 mg) was dissolved was added thiourea (760 mg), and the mixture was stirred at room temperature for 1 hour. Then, N-(4-(2,2-dicyanovinyl)phenyl-2,3,5,6-D4)acetamide (7-8) (2.1 g) was added thereto and the mixture was stirred under reflux for 3 hours. After the reaction was completed, the ethanol was removed off under reduced pressure. The residue was dissolved in warm water and weakly acidified with acetic acid. The precipitate was collected on a filter and dried to give 2.91 g of N-(4-(6-amino-5-cyano-2-mercapto-3,4-dihydropyrimidin-4-yl)phenyl-2,3,5,6-D4)-acetamide (7-9).
Yellow Powder.
$^1$H-NMR (DMSO-$d_6$) 9.99 (1H, s) 9.69 (1H, s) 6.13 (2H, 4.93 (1H, s) 2.07 (3H, s).

Methyl 3-(6-(4-(4-acetylaminophenyl-2,3,5,6-D4)-6-amino-5-cyanopyrimidin-2-ylthiomethyl)pyridin-2-yl)propionate (7-10)

N-(4-(6-Amino-5-cyano-2-mercapto-3,4-dihydropyrimidin-4-yl)phenyl-2,3,5,6-D4)acetamide (7-9) (2.91 g) was dissolved in dimethylformamide (60 ml). To the solution were added methyl 3-(6-methanesulfonyloxymethylpyridin-2-yl)propionate (2.73 g) and potassium carbonate (2.76 g), and the mixture was stirred at room temperature overnight. Then, N-bromosuccinimide (1.77 g) was added thereto, and the mixture was stirred for another 1 hour. After the reaction was completed, water was added to the reaction mixture and the mixture was extracted with ethyl acetate. The organic layer was dried over anhydrous magnesium sulfate, and concentrated in vacuo. The residue was purified by chromatography on silica gel (methylene chloride:methanol=20:1) to give 3.52 g of methyl 3-(6-(4-(4-acetylaminophenyl-2,3, 5,6-D4)-6-amino-5-cyanopyrimidin-2-ylthiomethyl)pyridin-2-yl)propionate (7-10).
White Powder.
$^1$H-NMR (DMSO-$d_6$) 10.26 (1H, s) 7.63 (1H, t, J=7.8 Hz) 7.36 (1H, d, J=7.8 Hz) 7.16 (1H, d, J=7.8 Hz) 4.46 (2H, s) 3.57 (3H, s) 2.99 (2H, t, J=7.2 Hz) 2.73 (2H, t, J=7.2 Hz) 2.09 (3H, s).

3-(6-(4-(4-Acetylaminophenyl-2,3,5,6-D4)-6-amino-5-cyanopyrimidin-2-ylthiomethyl)pyridin-2-yl)propionic acid (7-11)

Methyl 3-(6-(4-(4-acetylaminophenyl-2,3,5,6-D4)-6-amino-5-cyanopyrimidin-2-ylthiomethyl)pyridin-2-yl)-propionate (7-10) (3.52 g) was suspended in 50% water-containing acetonitrile (100 ml). To the suspension was added lithium hydroxide monohydrate (331 mg), and the mixture was refluxed for 2 hours. Then a solution of citric acid (1.59 g) in water (10 ml) was gradually added to the reaction mixture, and the reaction mixture was stirred at 50° C. for 1 hour. After cooling the reaction mixture, the precipitated crystal was collected on a filter, washed with water, and dried to give 2.29 g of 3-(6-(4-(4-acetylaminophenyl-2,3,5,6-D4)-6-amino-5-cyanopyrimidin-2-ylthiomethyl)pyridin-2-yl)propionic acid (7-11).
White Powder.
$^1$H-NMR (DMSO-$d_6$) 10.25 (1H, s), 7.64 (1H, t, J=7.8 Hz), 7.36 (1H, d, J=7.8 Hz), 7.16 (1H, d, J=7.8 Hz) 4.46 (2H, s) 2.92 (2H, t, J=7.2 Hz) 2.65 (2H, t, J=7.2 Hz) 2.09 (3H, s).

t-Butyl 4-(4-(3-(6-(4-(4-acetamidophenyl-2,3,5,6-D4)-6-amino-5-cyanopyrimidin-2-ylthio)methyl)pyridin-2-yl)-propanoyl)piperazin-1-yl)methyl)piperidine-1-carboxylate dihydrochloride (7-12)

3-(6-(4-(4-Acetylaminophenyl-2,3,5,6-D4)-6-amino-5-cyanopyrimidin-2-ylthiomethyl)pyridin-2-yl)propionic acid (7-11) (2.29 g) was suspended in acetone (46 ml). To the suspension were added 1-hydroxy-1H-benzotriazole (820 mg), 1-ethyl-3-(3-dimethylaminopropyl)-carbodiimide hydrochloride (1.16 g), and t-butyl 4-piperazin-1-ylmethyl-piperidine-1-carboxylate (1.43 g) in order, and the mixture was refluxed for 1 hour. The acetone was removed off in vacuo, and then ethyl acetate (23 ml) and water (23 ml) were added thereto, and the mixture was stirred for 30 minutes. The mixture was transferred into a separating funnel. The organic layer was washed with saturated aqueous sodium hydrogen carbonate and brine in order, dried over anhydrous magnesium sulfate and concentrated in vacuo. After the residue was completely dissolved in methanol (22.5 ml), conc. HCl (1.43 ml) was slowly added thereto dropwise at ice temperature and the mixture was stirred at room temperature for 1 hour. Then, ethanol (45 ml) was added thereto and the mixture was stirred at 50° C. for 1 hour. After cooling the reaction mixture, the precipitated crystal was collected on a filter, and dried to give 2.35 g of t-butyl 4-((4-(3-(6-((4-(4-acetamidophenyl-2,3,5,6-D4)-6-amino-5-cyanopyrimidin-2-ylthio)methyl)pyridin-2-yl)-propanoyl)piperazin-1-yl)methyl)piperidine-1-carboxylate dihydrochloride (7-12).
White Powder.
$^1$H-NMR (DMSO-$d_6$) 10.30 (1H, s) 7.95 (1H, m) 7.65 (1H, m) 7.45 (1H, m) 4.59 (2H, s) 4.40-4.31 (1H, m) 4.10-3.85 (3H, m) 3.70-3.30 (8H, m) 3.17-2.73 (8H, m) 2.09 (3H, s) 1.99 (1H, m) 1.78-1.74 (2H, m) 1.39 (9H, s).

N-(4-(6-Amino-5-cyano-2-(6-(3-oxo-3-(4-(piperidin-4-yl-methyl)piperazin-1-yl)propyl)pyridin-2-yl)methylthio)-pyrimidin-4-yl)phenyl-2,3,5,6-D4)acetamide trihydrochloride (7-13)

To t-butyl 4-(4-(3-(6-(4-(4-acetamidophenyl-2,3,5,6-D4)-6-amino-5-cyanopyrimidin-2-ylthio)methyl)pyridin-2-yl)-propanoyl)piperazin-1-yl)methyl)piperidine-1-carboxylate dihydrochloride (7-12) (2.35 g) was added 23 ml of hydrogen chloride [1 mol/L in ethyl acetate], and the mixture was stirred at room temperature for 24 hours. The precipitate was collected on a filter and washed with ethyl acetate (4.7 ml). The crude crystal was dissolved in water (10 ml) at room temperature, and filtrated. To the filtrate was slowly added acetone (40 ml), and the mixture was stirred with a seed crystal thereof for 2 hours. The precipitated crystal was collected on a filter, washed with acetone (4.7 ml), and then dried to give 1.93 g of N-(4-(6-amino-5-cyano-2-((6-(3-oxo-3-(4-(piperidin-4-ylmethyl)piperazin-1-yl)propyl)pyridin-2-yl)methylthio)pyrimidin-4-yl)phenyl-2,3,5,6-D4)acetamide trihydrochloride (7-13).
White Powder.
$^1$H-NMR (DMSO-$d_6$) 11.04 (1H, br-s) 10.38 (1H, s) 8.92-8.80 (2H, m) 8.10 (1H, m) 7.79 (1H, m) 7.59 (1H, m) 4.67 (2H, s) 4.37-4.33 (1H, m) 4.07-4.03 (1H, m) 3.70-2.82 (17H, m) 2.10-1.98 (6H, m) 1.48-1.37 (2H, m).

Hereinafter, processes of the following compounds are shown as reference examples.

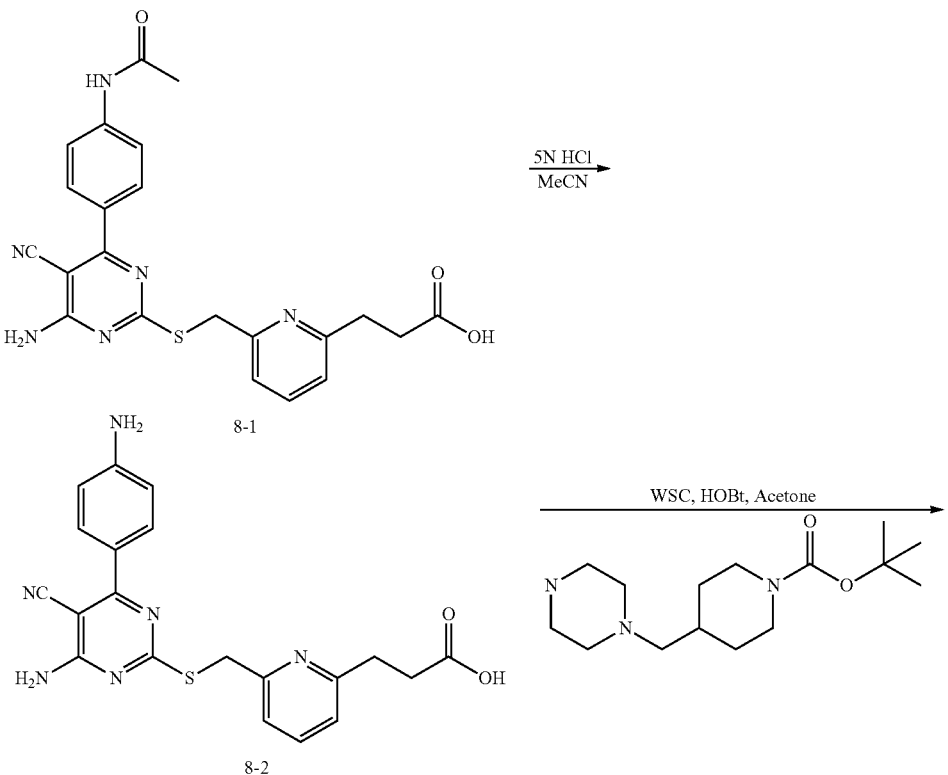

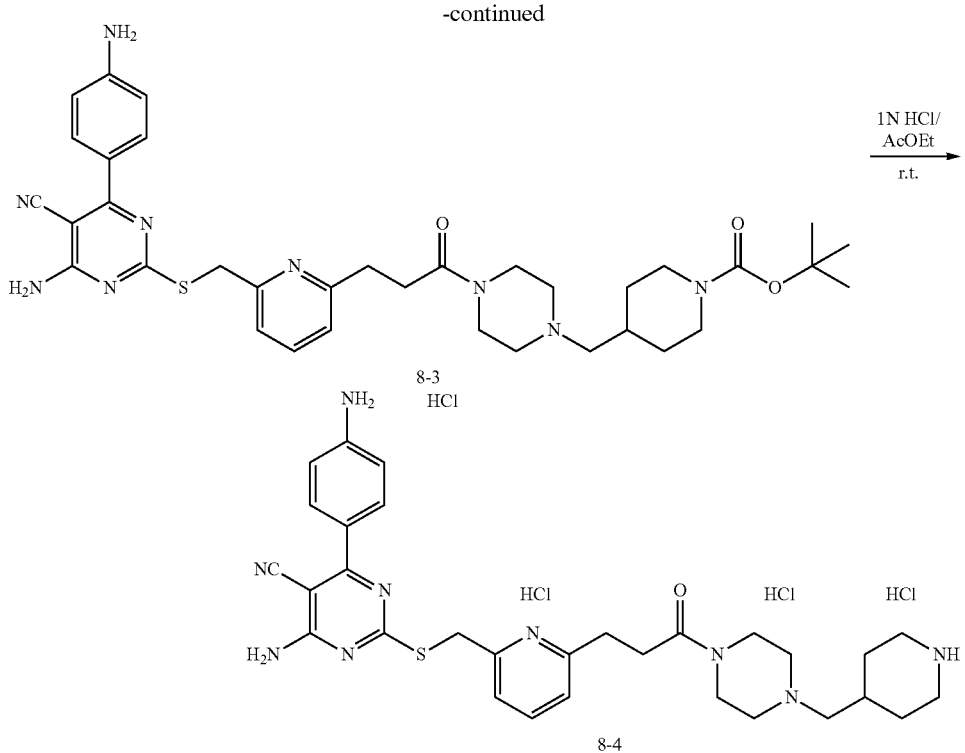

3-(6-(4-Amino-6-(4-aminophenyl)-5-cyanopyrimidin-2-ylthio-methyl)pyridin-2-yl)propionic acid (8-2)

3-(6-(4-(4-Acetylaminophenyl)-6-amino-5-cyanopyrimidin-2-ylthiomethyl)pyridin-2-yl)propionic acid (8-1) (230 mg) was suspended in acetonitrile (20 ml). To the suspension was added 5N hydrochloric acid (2 ml), and the mixture was stirred at 60° C. overnight. After cooling the reaction mixture, aqueous citric acid was gradually added thereto in order to neutralize the reaction mixture. The precipitated crystal was collected on a filter, washed with ethanol, and dried to give 150 mg of 3-(6-(4-amino-6-(4-aminophenyl)-5-cyanopyrimidin-2-ylthiomethyl)pyridin-2-yl)propionic acid (8-2).

Light Yellow Powder.

$^1$H-NMR (DMSO-$d_6$) 7.83 (2H, d, J=8.7 Hz) 7.74 (1H, t, J=7.5 Hz) 7.30 (1H, d, J=7.5 Hz) 7.12 (1H, d, J=7.5 Hz) 6.61 (2H, d, J=8.7 Hz) 5.90 (2H, br-s) 4.44 (2H, s) 2.91 (2H, t, J=7.5 Hz) 2.48 (2H, t, J=7.5 Hz).

t-Butyl 4-(4-(3-(6-((4-amino-6-(4-aminophenyl)-5-cyanopyrimidin-2-ylthio)methyl)pyridin-2-yl)propanoyl)piperazin-1-yl)methyl)piperidine-1-carboxylate (8-3)

3-(6-(4-Amino-6-(4-aminophenyl)-5-cyanopyrimidin-2-yl-sulfanylmethyl)pyridin-2-yl)propionic acid (8-2) (2.58 g) was suspended in acetone (50 ml). To the suspension were added 1-hydroxy-1H-benzotriazole (1.28 g), 1-ethyl-3-(3-dimethylaminopropyl)-carbodiimide hydrochloride (1.8 g), and t-butyl 4-piperazin-1-ylmethyl-piperidine-1-carboxylate (1.8 g) in order, and the mixture was refluxed for 1 hour. The acetone was removed off in vacuo, and then ethyl acetate (30 ml) and water (30 ml) were added thereto, and the mixture was stirred for 30 minutes. The mixture was transferred into a separating funnel. The organic layer was washed with saturated aqueous sodium hydrogen carbonate and brine in order, dried over anhydrous magnesium sulfate and concentrated in vacuo. The residue was purified by chromatography on silica gel (methylene chloride:methanol:28% aqueous ammonia=100:10:1) to give 3.9 g of t-butyl 4-(4-(3-(6-(4-amino-6-(4-aminophenyl)-5-cyanopyrimidin-2-ylthio) methyl)pyridin-2-yl)propanoyl)piperazin-1-yl)methyl)piperidine-1-carboxylate (8-3).

Light Yellow Powder.

$^1$H-NMR (CDCl$_3$) 7.95 (2H, d, J=8.7 Hz) 7.50 (1H, t, J=7.5 Hz) 7.28 (1H, d, J=7.5 Hz) 7.08 (1H, d, J=7.5 Hz) 6.71 (2H, d, J=8.7 Hz) 5.70 (2H, br-s) 4.51 (2H, s) 4.16-4.09 (4H, m) 3.59 (2H, t, J=4.8 Hz) 3.45 (2H, t, J=4.8 Hz) 3.13 (2H, t, J=7.5 Hz) 2.80 (2H, t, J=7.5 Hz) 2.75-2.65 (2H, m) 2.34-2.30 (4H, m) 2.13 (2H, d, J=7.2 Hz) 1.72-1.64 (1H, m) 1.46 (9H, s) 1.07-1.02 (2H, m).

4-Amino-6-(4-aminophenyl)-2-(6-(3-oxo-3-(4-(piperidin-4-yl-methyl)piperazin-1-yl)propyl)pyridin-2-yl)methylthio)-pyrimidine-5-carbonitrile tetrahydrochloride (8-4)

To t-butyl 4-(4-(3-(6-(4-amino-6-(4-aminophenyl)-5-cyanopyrimidin-2-ylthio)methyl)pyridin-2-yl)propanoyl)-piperazin-1-yl)methyl)piperidine-1-carboxylate (8-3) (3.6 g) was added 54 ml of hydrogen chloride [1 mol/L in ethyl acetate], and the mixture was stirred at room temperature for 24 hours. The precipitated crystal was collected on a filter, washed with ethyl acetate, and dried to give 4.3 g of 4-amino-6-(4-aminophenyl)-2-(6-(3-oxo-3-(4-(piperidin-4-ylmethyl)piperazin-1-yl)propyl)pyridin-2-yl)methylthio)-pyrimidine-5-carbonitrile tetrahydrochloride (8-4).

Light Yellow Powder.
¹H-NMR (DMSO-d$_6$) 11.23 (1H, br-s) 9.05 (1H, br-s) 8.93 (1H, br-s) 8.30 (1H, t, J=7.5 Hz) 7.79-7.68 (4H, m) 6.92 (2H, d, J=8.7 Hz) 4.77 (2H, s) 4.40-4.31 (8H, m) 3.36-3.18 (4H, m) 3.02-2.75 (6H, m) 2.21-1.98 (3H, m) 1.52-1.34 (2H, m).
Hereinafter, processes of the following compounds are shown as reference examples.
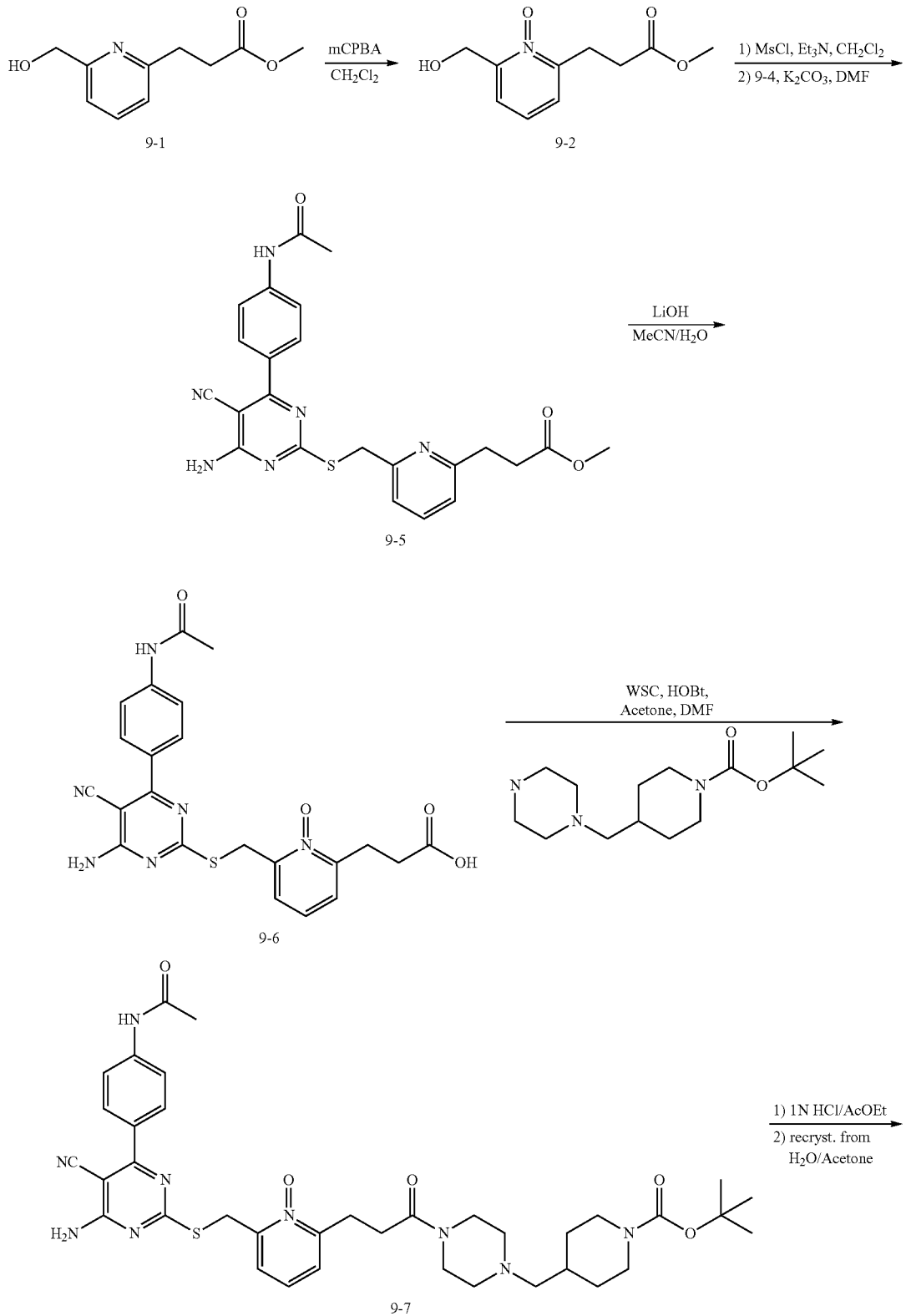

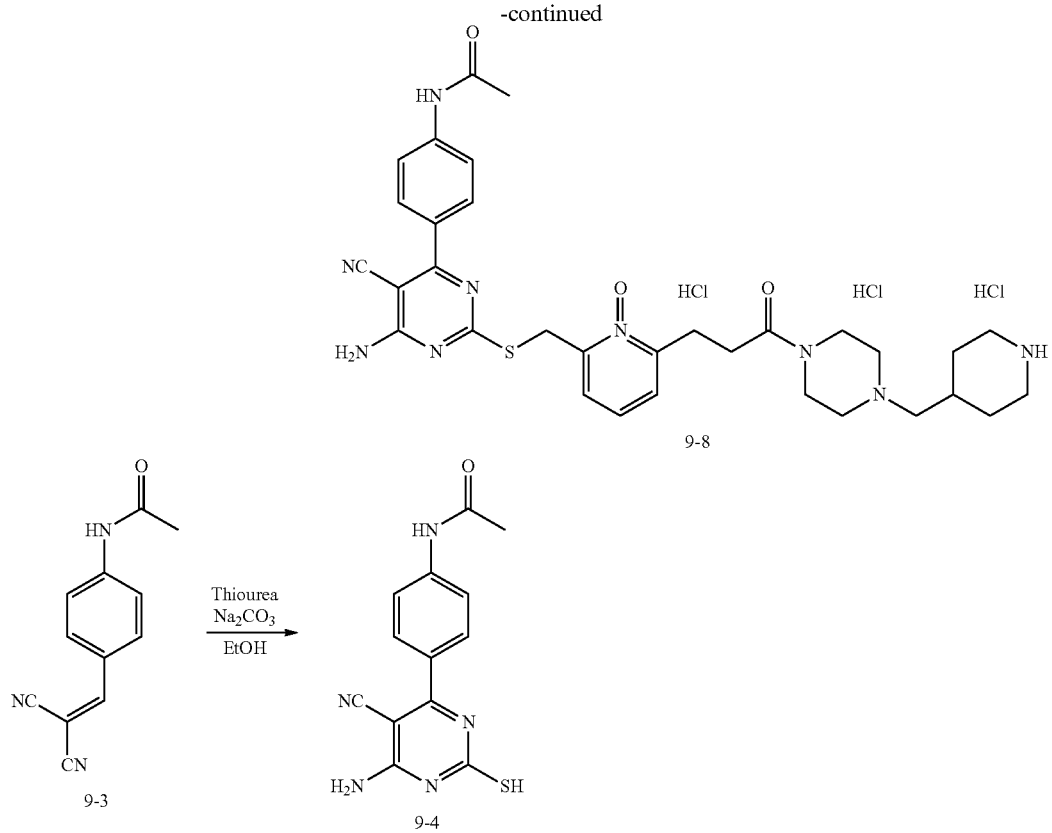

Methyl 3-(6-hydroxymethyl-1-oxy-pyridin-2-yl) propionate (9-2)

Methyl 3-(6-hydroxymethylpyridin-2-yl)propionate (9-1) (1.37 g) was dissolved in methylene chloride (15 ml), and a solution of m-chloroperbenzoic acid (1.46 g) in methylene chloride was slowly added thereto, and the mixture was stirred for 2 hours. The reaction solution was washed with 10% aqueous sodium sulfite, aqueous sodium hydrogen carbonate, and water in order. The organic layer was dried over anhydrous magnesium sulfate to give 880 mg of methyl 3-(6-hydroxymethyl-1-oxy-pyridin-2-yl)propionate (9-2). White Powder.

$^1$H-NMR (CDCl$_3$) 7.48-7.29 (1H, m) 7.25-7.22 (2H, m) 5.01 (1H, m) 4.80 (2H, S) 3.67 (3H, s) 3.23 (2H, t, J=7.2 Hz) 2.87 (2H, t, J=7.2 Hz).

N-(4-(6-Amino-5-cyano-2-mercaptopyrimidin-4-yl) phenyl)-acetamide (9-4)

Thiourea (1.52 g) was suspended in ethanol (15 ml), and then sodium carbonate (2.12 g) was added thereto, and the mixture was stirred at 60° C. for 30 minutes. Then, N-(4-(2,2-dicyanovinyl)phenyl)acetamide (9-3) (4.22 g) was added thereto and the mixture was stirred under reflux for 5 hours. After the reaction was completed, the ethanol was removed under reduced pressure. The residue was dissolved in warm water and weakly acidified with acetic acid. The precipitated crystal was collected on a filter, and dried to give 1.87 g of N-(4-(6-amino-5-cyano-2-mercaptopyrimidin-4-yl)phenyl)acetamide (9-4).

Yellow Powder.

$^1$H-NMR (DMSO-d$_6$) 10.29 (1H, s) 7.73 (2H, d, J=8.7 Hz) 7.64 (2H, d, J=8.7 Hz) 2.09 (3H, s).

Methyl 3-{6-[4-(4-acetylaminophenyl)-6-amino-5-cyanopyrimidin-2-ylsulfanylmethyl]-1-oxy-pyridin-2-yl}propionate (9-5)

Methyl 3-(6-hydroxymethyl-1-oxy-pyridin-2-yl)-propionate (9-4) (880 mg) was dissolved in methylene chloride (18 ml). To the solution was added triethylamine (1.15 ml), and the mixture was stirred at ice temperature for 10 minutes. Methanesulfonyl chloride (0.48 ml) was slowly added thereto dropwise, and the mixture was stirred at ice temperature for 30 minutes. To the reaction mixture was added water, and the mixture was transferred into a separating funnel. The organic layer was washed with saturated aqueous sodium hydrogen carbonate and brine. The organic layer was dried over anhydrous magnesium sulfate to give methyl 3-(6-methanesulfonyloxymethyl-1-oxy-pyridin-2-yl)propionate. Then, the compound was dissolved in dimethylformamide (10 ml), and N-(4-(6-amino-5-cyano-2-mercaptopyrimidin-4-yl)phenyl)acetamide (1.14 g) and potassium carbonate (1.1 g) were added thereto and the mixture was stirred at room temperature overnight. After the reaction was completed, water was added thereto. The precipitate was collected on a filter, and dried to give 580 mg of methyl 3-(6-(4-(4-acetylaminophenyl)-6-amino-5-cyano-pyrimidin-2-ylsulfanylmethyl)-1-oxy-pyridin-2-yl)-propionate (9-5).

White Powder.

$^1$H-NMR (DMSO-d$_6$) 10.26 (1H, s) 7.83 (2H, d, J=8.7 Hz) 7.74-7.69 (3H, m) 7.37 (1H, d, J=7.8 Hz) 7.23 (1H, t,

J=7.8 Hz) 4.50 (2H, s) 3.59 (3H, s) 3.05 (2H, t, J=7.2 Hz) 2.76 (2H, t, J=7.2 Hz) 2.09 (3H, s).

3-{6-[4-(4-Acetylaminophenyl)-6-amino-5-cyanopyrimidin-2-ylsulfanylmethyl]-1-oxy-pyridin-2-yl}propionic acid (9-6)

Methyl 3-{6-[4-(4-acetylaminophenyl)-6-amino-5-cyanopyrimidin-2-ylsulfanylmethyl]-1-oxy-pyridin-2-yl}propionate (9-5) (580 mg) was suspended in 50% water-containing acetonitrile (17 ml). To the suspension was added lithium hydroxide monohydrate (53 mg), and the mixture was stirred at 80° C. for 2 hours. Then, citric acid (253 mg) was added thereto, and the mixture was stirred at 50° C. for 1 hour. After cooling the reaction mixture, the precipitated crystal was collected on a filter, washed with water, and dried to give 540 mg of 3-{6-[4-(4-acetylaminophenyl)-6-amino-5-cyanopyrimidin-2-ylsulfanylmethyl]-1-oxy-pyridin-2-yl}propionic acid (9-6).
White Powder.
$^1$H-NMR (DMSO-$d_6$) 10.25 (1H, s) 7.83 (2H, d, J=8.7 Hz) 7.74-7.68 (3H, m) 7.37 (1H, d, J=7.8 Hz) 7.23 (1H, t, J=7.8 Hz) 4.50 (2H, s) 3.02 (2H, t, J=7.2 Hz) 2.67 (2H, t, J=7.2 Hz) 2.09 (3H, s).

t-Butyl 4-(4-(3-(6-(4-(4-acetamidophenyl)-6-amino-5-cyanopyrimidin-2-ylthio)methyl)-1-oxy-pyridin-2-yl)propanoyl)-piperazin-1-yl)methyl)piperidin-1-carboxylate (9-7)

3-{6-[4-(4-Acetylaminophenyl)-6-amino-5-cyanopyrimidin-2-ylsulfanylmethyl]-1-oxy-pyridin-2-yl}propionic acid (9-6) (520 mg) was dissolved in a mixture of acetone (10 ml) and dimethylformamide (10 ml). To the solution were added 1-hydroxy-1H-benzotriazole (224 mg), 1-ethyl-3-(3-dimethylaminopropyl)-carbodiimide hydrochloride (318 mg), t-butyl 4-piperazin-1-ylmethyl-piperidine-1-carboxylate (315 mg) in order, and the mixture was refluxed for 2 hours. The acetone was removed off in vacuo, and then ethyl acetate and water were added thereto, and the mixture was stirred for 30 minutes. The mixture was transferred into a separating funnel, and the organic layer was washed with saturated aqueous sodium hydrogen carbonate and brine in order, dried over anhydrous magnesium sulfate and concentrated in vacuo. The residue was purified by chromatography on silica gel (methylene chloride:methanol=50:1) to give 470 mg of t-butyl 4-(4-(3-(6-(4-(4-acetamidophenyl)-6-amino-5-cyanopyrimidin-2-ylthio)methyl)-1-oxy-pyridin-2-yl)propanoyl)piperazin-1-yl)methyl)-piperidine-1-carboxylate (9-7).
White Powder.
$^1$H-NMR (CDCl$_3$) 7.98 (2H, d, J=8.7 Hz) 7.69-7.61 (3H, m) 7.43 (1H, dd, J=7.8, 1.8 Hz) 7.31 (1H, dd, J=7.8, 1.8 Hz) 7.09 (1H, t, J=7.8 Hz) 5.75 (2H, s) 4.65 (2H, s) 4.12-4.00 (2H, m) 3.55 (2H, br-s) 3.46 (2H, br-s) 3.24 (2H, t, J=7.2 Hz) 2.87 (2H, t, J=7.2 Hz) 2.71-2.63 (2H, m) 2.32-2.29 (4H, m) 2.23 (3H, s) 2.11 (2H, d, J=6.9 Hz) 1.71-1.67 (3H, m) 1.46 (9H, s) 1.07-0.97 (2H, m).

N-(4-(6-Amino-5-cyano-2-((6-(3-oxo-3-(4-(piperidin-4-yl-methyl)piperazin-1-yl)propyl)-1-oxy-pyridin-2-yl)methyl-thio)pyrimidin-4-yl)phenyl)acetamide trihydrochloride (9-8)

To t-butyl 4-(4-(3-(6-(4-(4-acetamidophenyl)-6-amino-5-cyanopyrimidin-2-ylthio)methyl)-1-oxypyridin-2-yl)-propanoyl)piperazin-1-yl)methyl)piperidine-1-carboxylate (450 mg) was added 4.5 ml of hydrogen chloride [1 mol/L in ethyl acetate], and the mixture was stirred at room temperature for 24 hours. The precipitate was collected on a filter, washed with ethyl acetate, and dried to give a white crude crystal. The crude crystal was dissolved in water (2.5 ml) at room temperature, and filtrated. To the filtrate was slowly added acetone (10 ml), and the mixture was stirred for 6 hours. The precipitated crystal was collected on a filter, washed with acetone, and then dried to give 230 mg of N-(4-(6-amino-5-cyano-2-((6-(3-oxo-3-(4-(piperidin-4-yl-methyl)piperazin-1-yl)propyl)-1-oxy-pyridin-2-yl)methyl-thio)pyrimidin-4-yl)phenyl)acetamide trihydrochloride.
White Powder.
$^1$H-NMR (DMSO-$d_6$) 10.65 (1H, m) 10.33 (1H, s) 8.80-8.66 (2H, m) 7.82 (2H, d, J=8.7 Hz) 7.75-7.69 (3H, m) 7.43 (1H, d, J=7.8 Hz) 7.25 (1H, t, J=7.8 Hz) 4.50 (2H, s) 4.42-4.38 (1H, m) 4.18-4.09 (1H, m) 3.74-3.25 (8H, m) 3.08-3.01 (4H, m) 2.87-2.70 (4H, m) 2.09 (3H, s) 2.08-1.97 (2H, m) 1.47-1.39 (2H, m).

Hereinafter, some examples of pharmaceutical compositions comprising the present compounds are shown.

Example 8

To a 5 L stainless beaker was added purified water (about 4.5 kg). Concentrated glycerin (130 g) as an isotonic agent and succinic acid (3.5 g) as a buffer were added thereto, and the mixture was stirred to be dissolved. Then, N-(4-(6-amino-5-cyano-2-((6-(3-oxo-3-(4-(piperidin-4-ylmethyl) piperazin-1-yl)propyl)pyridin-2-yl)methylthio)-pyrimidin-4-yl)phenyl)acetamide (the compound of Example 1) (0.5 g) was added to the solution, and the mixture was stirred to be dissolved. To the solution was added benzododecinium bromide (0.3 g) as a preservative, and the mixture was gently stirred. The complete dissolution was visually confirmed. To the solution was gradually added 4% (w/w) aqueous sodium hydroxide to adjust the pH to 6.6. After adjusting pH, purified water was added to the solution to make the total weight 5.0 kg, and the solution was gently stirred. The solution was aseptically filtrated, then the filtrate was aseptically put into an eye drop bottle and the bottle was sealed.

Example 9

A pharmaceutical composition of Example 9 was prepared using sodium dihydrogen phosphate (3.00 g) as a buffer instead of succinic acid in a similar manner to Example 8.

Example 10

A pharmaceutical composition of Example 10 was prepared using glucose (275 g) as an isotonic agent instead of concentrated glycerin in a similar manner to Example 8.

Example 11

A pharmaceutical composition of Example 11 was prepared using mannitol (255 g) as an isotonic agent instead of concentrated glycerin in a similar manner to Example 8.

Example 12

A pharmaceutical composition of Example 12 was prepared using concentrated glycerin (68 g) and propylene glycol (50 g) as an isotonic agent instead of concentrated glycerin in a similar manner to Example 8.

Example 13

A pharmaceutical composition of Example 13 was prepared using concentrated glycerin (105 g) and sorbitol (43 g) as an isotonic agent instead of concentrated glycerin in a similar manner to Example 8.

Example 14

A pharmaceutical composition of Example 14 was prepared using propylene glycol (50 g), mannitol (100 g) and sorbitol (43 g) as an isotonic agent instead of concentrated glycerin in a similar manner to Example 8.

Example 15

A pharmaceutical composition of Example 15 was prepared using benzalkonium chloride (0.5 g) as a preservative instead of benzododecinium bromide in a similar manner to Example 8.

Hereinafter, the examples of the pharmacological tests using the compounds of the invention are described.

Test 1: c-AMP Generating Action in Cell Expressing Adenosine A2a Receptor

The test was carried out as mentioned below with reference to the method disclosed in the reference (Klotz k. N. et al., Naunyn-Schmiedeberg's Arch. Pharmacol., (1998) 357, 1-9; Shryock J. C. et al., Molecular Pharmacology, (1998) 53, 886-893).

As to the cell to be used in the test, HEK293 cell expressing adenosine A2a receptor (Human) (PerkinElmer Life Sciences, Code No. RBHA2AC) was used.

As to the culture medium, Dulbecco's modified Eagles medium (DMEM) including 10% FBS (Fetal bovine serum) and 1 mM of sodium pyruvate was used.

The cell was placed on 96 well plate ($1 \times 10^5$/well), and cultured overnight. After removing off the supernatant, 0.1 ml of DMEM (without FBS) containing 20 mM HEPES, 0.1 mM IBMX (3-isobutyl-1-methylxanthine) and 2 unit/mL adenosine deaminase were added to each well, and they were incubated at 37° C. for 30 minutes. Then, 0.1 ml of the culture medium containing the DMSO solution of the test compound in the predetermined concentration was added to each well, and they were incubated for additional 30 minutes. After removing off the supernatant, the cytolytic solution was added thereto to quench the reaction. The amount of c-AMP in each well was measured by using the c-AMP enzyme immunoassay (EIA) system (Amersham Biosciences, Code No. RPN225).

The same assay was repeated using CGS-21680 (2-p-carboxyethyl)phenethylamino-5'-N-ethylcarboxamidoadenosine hydrochloride, (Sigma, code C141) as a reference compound.

The amount of resultant c-AMP in the reference medium, caused by 1 µM of the reference compound, was defined to be 100%. The amount of resultant c-AMP in each test medium was measured, and the concentration producing 50% c-AMP amount was calculated based on the results of each test compound in the predetermined concentration, which is defined as $EC_{50}$ value.

The above test results obtained using the following compounds of the invention prepared in the above-mentioned examples are shown in the following Table.

Result

| Example | A2a agonistic activity ($EC_{50}$, nM) |
|---------|----------------------------------------|
| 1       | 3.3                                    |
| 2       | 2.9                                    |
| 3       | 1.8                                    |
| 4       | 6.1                                    |
| 5       | 8.4                                    |

Test 2: Effect of the Compound of Example 1 to Corneal Epithelium Cell

[Method]

Rabbit corneal epithelium cell (KURABO) was used as the cell for the test. To the rabbit corneal epithelium cell placed on 96 well plate was added the compound of Example 1, and the sample was incubated for 60 minutes. Then, the sample was irradiated with UVA (3.5 mW/cm$^2$) for 70 minutes using a solar simulator (SOL500). After that, the cell was washed with a buffer. After 24 hours, the cell viability was evaluated by the neutral red uptake assay.

[Result]

The result is shown in FIG. 1. The cell viabilities after the addition of the compound of Example 1 (0.25, 0.5 and 1 mM) and then the irradiation with the solar simulator were 106.3%, 115.0% and 100.7%, respectively, and thus the decrease of the cell viability was not observed at all.

From the above result, it is obvious that the present preparation can be used in a high concentration even outdoors in the sunshine since the present compound did not exhibit any cytotoxicity even in using it in a high concentration, and the present preparation is a medicament which can be safely used.

Test 3: Vascular Relaxation

Ocular circulatory disorder occurs in glaucoma, retinitis pigmentosa, macular degeneration, ischemic optic neuropathy, retinal artery occlusion, retinal vein occlusion, diabetic retinopathy, and iridocyclitis. Especially, circulatory disorder in optic nerve head is considered an important factor in glaucoma.

Ocular blood flow has two circulatory systems. One is a route through ciliary artery and the other is a route through central retinal artery. Ciliary artery passes to arteries in choroid, optic nerve head, iris, and ciliary body. On the other hand, central retinal artery passes to artery in retina, and a part of central retinal artery branches to arteriole in optic nerve head.

The compound of Example 1, relaxes ciliary artery, is considered to improve ocular blood flow. Therefore the compound of Example 1 is expected to be an effective drug for therapy of diseases of eye such as glaucoma, retinitis pigmentosa, macular degeneration, ischemic optic neuropathy, retinal artery occlusion, retinal vein occlusion, diabetic retinopathy, and iridocyclitis.

<Material and Method>

Rabbits were sacrificed with an overdose of sodium pentobarbital by intravenous administration. The eyes were enucleated and ciliary arteries were isolated. Vascular rings were cut 2 mm in length from ciliary arteries and set to Danish Multi Myograph System 610M (Danish myo technology) under microscopic observation. The vessels were equilibrated in oxygenated krebs solution with 5% $CO_2$ and 95% $O_2$ at 37° C.

To confirm the endothelium damage of vessels, the relaxation of ciliary artery by 100 µM carbachol was tested. If relaxation by carbachol was more than 30%, the vessels whose endothelium had no damage were used for the experiments.

After ciliary artery was contracted with High K$^+$-krebs solution, the compound of Example 1 was serially administrated to chamber from 0.3 μM to 300 μM. The tension was measured by Myodaq ver 2.01 (Danish myo technology).
<Result>

Figure 2:
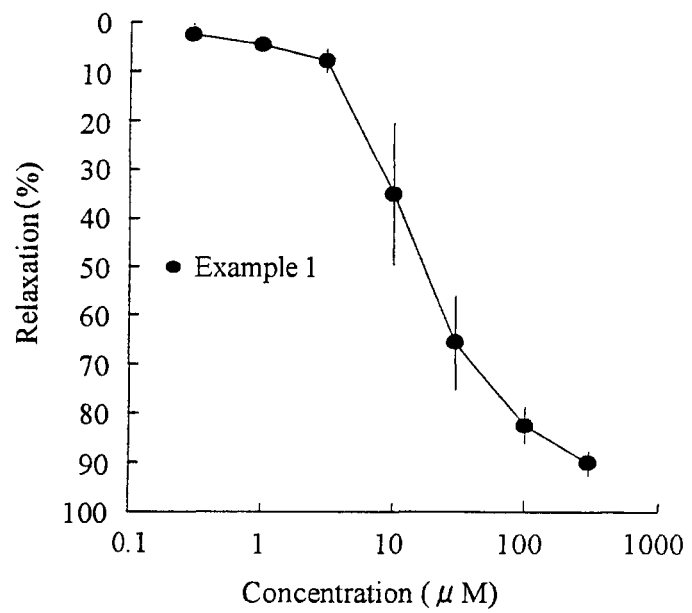
FIG. 2 shows the effects of the compound of Example 1 on ciliary artery in rabbits.

The results are shown in the following table and FIG. 2. The compound of Example 1 dose-dependently relaxed ciliary artery in rabbits, and its $EC_{50}$ was 17.0 μM. Therefore it is concluded that the compound of Example 1 shows relaxation in ciliary artery.

| Concentration (μM) | Relaxation (%) |
|---|---|
| 0.3 | 2.6 ± 0.5 |
| 1 | 4.8 ± 1.2 |
| 3 | 7.9 ± 2.3 |
| 10 | 35.3 ± 14.4 |
| 30 | 65.6 ± 9.5 |
| 100 | 82.4 ± 3.7 |
| 300 | 90.1 ± 2.4 |

Test 4: Neuroprotection

In glaucoma, one of the diseases of eye leading to blindness, retinal ganglion cell (RGC) is selectively injured. Subsequently the optic nerve is injured, and finally the visual field defect is appeared. Retinal artery occlusion, retinal vein occlusion, diabetic retinopathy and ischemic optic neuropathy are also diseases of eye related optic nerve disorder. In addition, macular degeneration, retinitis pigmentosa and Leber's hereditary optic neuropathy are diseases of eye related the damage of neuronal cell in retina.

The compound of Example 1, shows the neuroprotective effects on RGC, is expected to be neuroprotective drug that is used for therapy of diseases of eye such as retinal artery occlusion, retinal vein occlusion, diabetic retinopathy, ischemic optic neuropathy, macular degeneration, retinitis pigmentosa and Leber's hereditary optic neuropathy.
<Material and Method>

This experiment was performed according to a method reported by Otori et al. (Invest Opthalmol Vis Sci. 39: 972-981, 1998).

Eyes were enucleated from 7 day old Long Evans rat. Retinas were isolated from the eyes. The retinas were dissociated by incubating with Neurobasal medium including 15 U/mL papain at 37° C. for 30 minutes. The retinal suspension was prepared.

The retinal suspension was incubated in anti-SIRP antibody (Chemicon)-coated flask at room temperature for 30 minutes. The non adherent cells were placed in anti-thy-1 antibody (Chemicon)-coated flask. The cells were incubated at room temperature for 30 minutes. Finally the adherent cells in flask were washed with Neurobasal medium. After centrifugation at 800 rpm for 5 minutes, the purified RGC was prepared. The cells were seeded on glass coverslips that had been coated with poly-L-lysine and laminin. The purified RGC were cultured in Neurobasal medium containing B27 supplement, 1 mM glutamine 50 ng/mL CNTF, 10 μM Forskolin. Culture was maintained at 37° C. in humidified atmosphere containing 5% $CO_2$ and 95%, air. BDNF (50 ng/mL) or the compound of Example 1 at final concentration of 0 nM (control), 3 nM, 10 nM or 30 nM was administered immediately after cell seeding.

Cell survival (cell viability) was determined by counting stained RGC. Five days after culture started, RGC were stained with 1 μM Calcein-AM (Molecular probe). The number of RGC was counted using fluorescence microscope. The percentage of cell survival (cell viability) was calculated by using the counts of control group as 0%, and the counts of BDNF group as 100%.
<Result>

Figure 3:
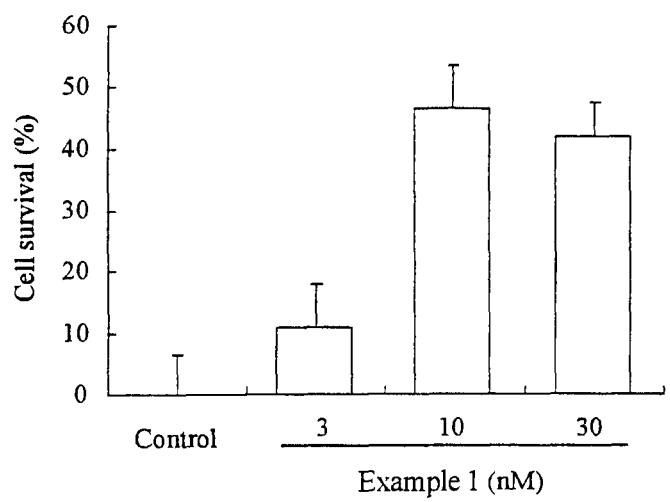
FIG. 3 shows the effect of the compound of Example 1 on cell survival in Rat Retinal Granglion Cell.

The results are shown in the following table and FIG. 3. The compound of Example 1 showed increase in cell survival dose-dependently. This result suggested that the compound of Example 1 had the neuroprotective effects on RGC.

| Groups | n | Cell survival (%) |
|---|---|---|
| Control | 8 | 0.0 ± 6.5 |
| Example 1 3 nM | 8 | 10.9 ± 7.0 |
| Example 1 10 nM | 8 | 46.5 ± 7.0 |
| Example 1 30 nM | 8 | 41.9 ± 5.5 |

Data = Mean ± SE

The cell survival was calculated by using the counts of control groups as 0% and the counts of BDNF groups as 100%.

The invention claimed is:

1. A compound of formula (1):

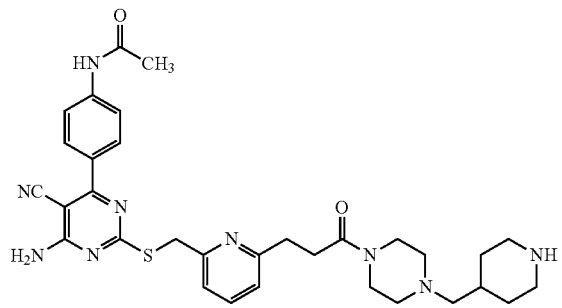

or a salt thereof.

2. The compound according to claim 1, wherein the compound is N-(4-(6-amino-5-cyano-2-((6-(3-oxo-3-(4-(piperidin-4-ylmethyl)piperazin-1-yl)propyl)pyridine-2-yl)methylthio)pyrimidine-4-yl)phenyl)acetamide.

3. A pharmaceutical composition comprising the compound of claim 1 or a salt thereof, and a pharmaceutically acceptable carrier.

4. An aqueous liquid preparation comprising the pharmaceutical composition of claim 3.

5. The aqueous liquid preparation of claim 4 which further comprises one of more additives selected from a pharmaceutically acceptable buffer, isotonic agent, preservative, solubilizer and pH adjuster.

6. The aqueous liquid preparation of claim 5 wherein the buffer is selected from succinic acid, boric acid, phosphoric acid, amino acid and a pharmaceutically acceptable salt thereof.

7. The aqueous liquid preparation of claim 6 wherein the buffer is succinic acid.

8. The aqueous liquid preparation of claim 5 wherein the isotonic agent is one or two isotonic agents selected from glucose, sorbitol, mannitol, sodium chloride, potassium chloride, propylene glycol and glycerin.

9. The aqueous liquid preparation of claim 5 wherein the preservative is selected from benzalkonium chloride, benzethonium chloride, benzododecinium bromide, chlorhexidine gluconate, methyl para-oxybenzoate, propyl para-oxybenzoate, chlorobutanol and benzyl alcohol.

10. The aqueous liquid preparation of claim 5 wherein the pH is about 5.0 to 9.0.

11. N-(4-(6-amino-5-cyano-2-((6-(3-oxo-3-(4-piperidin-4-ylmethyl)piperazin-1-yl)propyl)pyridine-2-yl)methylthio)pyrimidine-4-yl)phenyl)acetamide trihydrochloride.

12. A method for treating or preventing an eye disease in an animal or human in need thereof comprising administering to said animal or human an effective amount of the compound of claim 1 or a salt thereof,
wherein the effective amount is such that the compound agonizes the adenosine A2a receptor.

13. The method of claim 12 for treating or preventing glaucoma.

* * * * *